US007419961B2

(12) United States Patent
Napoletano et al.

(10) Patent No.: US 7,419,961 B2
(45) Date of Patent: Sep. 2, 2008

(54) 9A-AZALIDES WITH ANTI-INFLAMMATORY ACTIVITY

(75) Inventors: Mauro Napoletano, Milan (IT); Andrea Mereu, Como (IT); Ermanno Moriggi, Busto Arsizio (IT); Fernando Ornaghi, Carlazzo (IT); Gabriele Morazzoni, Lainate (IT); Franco Pellacini, Milan (IT)

(73) Assignee: Zambon S.p.A., Bresso (IT)

( * ) Notice: Subject to any disclaimer, the term of this patent is extended or adjusted under 35 U.S.C. 154(b) by 122 days.

(21) Appl. No.: 10/531,462

(22) PCT Filed: Oct. 28, 2003

(86) PCT No.: PCT/EP03/12071

§ 371 (c)(1),
(2), (4) Date: Apr. 15, 2005

(87) PCT Pub. No.: WO2004/039821

PCT Pub. Date: May 13, 2004

(65) Prior Publication Data

US 2006/0166904 A1    Jul. 27, 2006

(30) Foreign Application Priority Data

Oct. 29, 2002   (IT) .......................... MI2002A2292

(51) Int. Cl.
*A61K 31/70*     (2006.01)
*C07H 17/08*    (2006.01)
(52) U.S. Cl. .......................................... 514/29; 536/7.4
(58) Field of Classification Search .................. 536/7.4; 514/29
See application file for complete search history.

(56) References Cited

U.S. PATENT DOCUMENTS

| 3,478,014 | A |   | 11/1969 | Djokic et al. |
|---|---|---|---|---|
| 3,928,387 | A |   | 12/1975 | Kierstead et al. |
| 4,328,334 | A |   | 5/1982 | Kobrehel et al. |
| 4,464,527 | A |   | 8/1984 | Bright |
| 4,886,792 | A |   | 12/1989 | Djokic et al. |
| 5,250,518 | A |   | 10/1993 | Kobrehel et al. |
| 6,262,030 | B1 | * | 7/2001 | Wu et al. ....................... 514/29 |
| 6,455,576 | B1 |   | 9/2002 | Pellacini et al. |

FOREIGN PATENT DOCUMENTS

| BE | 892357 | 7/1982 |
|---|---|---|
| EP | 0 771 564 | 5/1997 |
| EP | 0 775 489 | 5/1997 |
| EP | 20010301 | 4/2001 |
| WO | 92/16226 | 10/1992 |
| WO | 00/42055 | 7/2000 |

OTHER PUBLICATIONS

M. T. Labro: Anti-inflammatory activity of macrolides: a new therapeutic potential? Journal of Antimicrobial Chemotherapy, vol. 41, Suppl. B, pp. 37-46, 1998.
Jun Tamaoki: "Effect of Erythromycin on Endotoxin-induced Microvascular Leakage in the Rat Trachea and Lungs" Am. J. Respir. Crit. Care Med., vol. 151, pp. 1582-1588, 1995.
Vera M. Keatings: "Differences in Interleukin-8 and Tumor Necrosis Factor-α in Induced Sputum from Patients with Chronic Obstructive Pulmonary Disease or Asthma" Am. J. Respir. Crit. Care Med., vol. 153, pp. 530-534, 1996.
Hajime Takizawa: "Erythromycin Modulates IL-8 Expression in Normal and Inflamed Human Bronchial Epithelial Cells" Am. J. Respir. Crit. Care Med., vol. 156, pp. 266-271, 1997.
Hiroyuki Miyatake et al.: "Erythromycin Reduces the Severity of Bronchial Hyperresponsiveness in Asthma" Chest, vol. 99, pp. 670-673, 1991.
Peter J. Barnes: "Mechanisms in COPD, Differences From Asthma" Chest, vol. 117, 2 Suppl., pp. 10S-14S, 2000.
Tomoko Suzuki: "Erythromycin and Common Cold in COPD" Chest, vol. 120, pp. 730-733, 2001.
Maric Therese Labro: "Immunomodulatory Actions of Antibacterial Agents" Clin. Immunother., vol. 6, pp. 454-464, 1996.
Slobodan Djokic et al.: "Erythromycin Series. Part 11. Ring Expansion of Erythromycin A Oxime by the Beckmann Rearrangement" J. Chem. Soc. Perkin Trans., pp. 1881-1890, 1986.
Viera Stvrtinova, Jan Jakubovsky and Ivan Hulin: "Inflammation and Fever" Academic Electronic Press, 1995.
Ronald Anderson: "Membrane-Stabilizing, Anti-Inflammatory Interactions of Macrolides With Human Neutrophils" Inflammation, vol. 20, No. 6, pp. 693-705, 1996.
Edwin H. Flynn: "Erythromycin. I. Properties and Degradation Studies" J. Am. Chem. Soc., vol. 76, pp. 3121-3131, 1954.
Jean-Claude Gasc et al.: "New Ether Oxime Derivatives of Erythromycin A, A Structure-Activity Relationship Study" The Journal of Antibiotics, vol. 44, pp. 313-330, 1991.
Crystal C. Koch: "Apoptosis, oxidative metabolism and interleukin-8 production in human neutrophils exposed to azithromycin: effects of *Streptococcus pneumoniae*" Journal of Antimicrobial Chemotherapy, vol. 46, pp. 19-26, 2000.
Melita Zunic: "MDP(Lysyl)GDP, a Nontoxic Muramyl Dipeptide Derivative, Inhibits Cytokine Production by Activiated Macrophages and Protects Mice from Phrobol Ester- and Oxazolone-Induced Inflammation" The Society for Investigative Dermatology, Inc., vol. 111, No. 1, pp. 77-82, 1998.

(Continued)

*Primary Examiner*—Elli Peselev
(74) *Attorney, Agent, or Firm*—Oblon, Spivak, McClelland, Maier & Neustadt, P.C.

(57) ABSTRACT

Macrolides with anti-inflammatory activity are described. Particularly described are 9a-azalides and their anti-inflammatory activity without cladinose in position 3, the pharmaceutically acceptable salts thereof and the pharmaceutical composition that contain them as active principle.

15 Claims, No Drawings

OTHER PUBLICATIONS

Shin-ichi Konno: "Inhibition of Human T-Lymphocyte Activation by Macrolide Antibiotic, Roxithromycin" Life Sciences, vol. 51, pp. PL 231-236, 1992.

Partrick R. Murray, Ellen Jo Baron, Michael A. Pfaller, Fred C. Tenover and Robert H. Yolken: "Manual of Clinical Microbiology" American Society for Microbiology, 7th Edition, 1999.

Houria Abdelghaffar: "Erythromycin A-Derived Macrolides Modify the Functional Activities of Human Neutrophils by Altering the Phospholipase D-Phosphatidate Phosphohydrolase Transduction Pathway" The Journal of Immunology, vol. 159, pp. 3395-4005, 1997.

Adam Jaffe: "Long-term azithromycin may improve ling function in children with cystic fibrosis" The Lancet, vol. 351, p. 420, Feb. 7, 1998.

The Merck Index, XIII edition, No. 917, p. 159, 2001.

Hiroshi Koyama, Duncan M. Geddes: "Erythromycin and diffuse panbrochiolitis" Thorax, vol. 52, pp. 915-918, 1997.

* cited by examiner

9A-AZALIDES WITH ANTI-INFLAMMATORY ACTIVITY

The application is a 371 of PCT/EP03/12071 filed on Oct. 28, 2003.

DESCRIPTION

The present invention relates to macrolides with anti-inflammatory activity, and more particularly it relates to 9a-azalides without cladinose in position 3 with anti-inflammatory activity, their pharmaceutically acceptable salts and pharmaceutical compositions that contain them as active principle.

It is known that in addition to their antibiotic properties, many antibiotics also possess anti-inflammatory properties [Clin. Immunother., 1996, 6, 454-464].

Azithromycin (The Merck Index, XIII edition, No. 917, page 159) is the prototype of a class of antibiotic macrolides commonly called azalides that are widely used in the treatment of infections of the upper and lower respiratory passages, of odontostomatologic infections, infections of the skin and soft tissues, and in nongonococcal urethritis (caused by *Chlamydia trachomatis*).

Compared with the classic macrolides, the azalides possess a broad spectrum of action, better tissue penetration, and a half-life such that a single daily administration is sufficient.

The interest of the scientific community has recently turned towards the immunomodulating and anti-inflammatory activities of the macrolide antibiotics [Journal of Antimicrobial Chemotherapy, 1998, 41, Suppl. B, 37-46].

These activities have been well documented both by clinical studies and by experiments in vivo and in vitro.

The macrolides have proved useful in the treatment of inflammatory pathologies such as panbronchiolitis [Thorax, 1997, 52, 915-918], bronchial asthma [Chest, (1991), 99, 670-673], COPD (CHEST 2001, 120, 730-733) and azithromycin in particular has proved effective in improving lung function in patients with cystic fibrosis [The Lancet, (1998), 351, 420].

The in-vitro activity of the macrolides has been found to be particularly effective in modulating the metabolic functions of some cells of the immune system such as neutrophils [The Journal of Immunology, 1997, 159, 3395-4005] and T lymphocytes [Life Science, 1992, 51, PL 231-236] and in the modulation of inflammation mediators such as interleukin 8 (IL-8) [Am. J. Respir. Crit. Care Med., (1997), 156, 266-271] or interleukin 5 (IL-5) (patent applications EP 0775489 and EP 0771564, in the name of Taisho Pharmaceutical Co., Ltd.).

The neutrophils, in particular, constitute the first cell line recruited at the site of infection or tissue lesion in the very first phases of an inflammatory response.

A nonphysiologic accumulation of neutrophils in the inflamed tissue, their activation, the subsequent release of proteases and the increase in production of reactive metabolites of oxygen characterize some forms of inflammatory response which, in most cases, degenerate into pathologic conditions.

Thus, even though the neutrophils are essential in the immune defense and in the inflammatory process, they are known to be implicated in pathologies that derive from the majority of chronic inflammatory conditions and from lesions through ischemic reperfusion (Inflammation and Fever; Viera Stvrtinovà, Jan Jakubovsky and Ivan Hùlin; Academic Electronic Press, 1995).

This same document describes the pathologies for which the influence of an altered functionality of the neutrophils on their genesis and/or on their development has been proven: these included atherosclerosis, damage from ischemic reperfusion, rheumatoid arthritis, vasculitis and glomerulonephritis of autoimmune origin and chronic pulmonary inflammations such as ARDS (adult respiratory distress syndrome). COPD (chronic obstructive pulmonary disease) is a chronic pathology characterized by inflammation and progressive destruction of lung tissue caused by the massive presence of activated neutrophils with consequent release of metalloproteinases and increase in the production of oxygen radicals [Am. J. Respir. Crit. Care Med., 1996, 153, 530-534] [Chest, 2000, 117 (2 Suppl.), 10S-14S].

The administration of macrolides to asthmatics is accompanied by a reduction in hypersecretion and in bronchial hypersensitivity resulting from their anti-oxidative and anti-inflammatory interaction with phagocytes and in particular with neutrophils; this interaction would prevent many bioactive lipids, involved in the pathogenesis of bronchial asthma, from exerting their membrane-destabilizing, pro-inflammatory activity (Inflammation, Vol. 20, No. 6, 1996).

In the description of patent application HR20010301 in the name of Pliva, there is a good description of the anti-inflammatory activity of azithromycin, a known antibacterial agent.

This includes confirmation of the ability of the azalide to induce apoptosis in human neutrophils in vitro, as already reported in the literature [J. Antimicrob. Chemother., 2000, 46, 19-26] and provides evidence that its anti-inflammatory activity is in line with what has been described for the classic macrolides (lactone rings with 14 members); in particular, it has been demonstrated that the administration of azithromycin promotes degranulation of human neutrophils, inhibits the production of reactive species of oxygen in the stimulated neutrophils and, moreover, inhibits the release of interleukin 8 which is a potent neutrophil-specific activating and chemiotactic factor.

The distinctive therapeutic efficacy of the macrolides in pathologies in which the traditional anti-inflammatory drugs, for example corticosteroids, have proved ineffective [Thorax, (1997), 52, 915-918, already cited] justifies the considerable interest in this new potential class of anti-inflammatory drugs.

However, the fact that the classic macrolides possess a potent antibacterial activity does not mean they can be used more widely in the long-term treatment of inflammatory processes not caused by pathogenic microorganisms; this could in fact cause the rapid development of resistant strains.

It would therefore be desirable to have new substances with macrolide structure that exhibit anti-inflammatory activity but at the same time do not have antibiotic properties.

Some classes of macrolide derivatives that have anti-inflammatory activity are described in the literature.

For example, the already cited European patent application in the name of Taisho claims erythromycin derivatives modified in positions 3, 9, 11 and 12, as potent inhibitors of IL-5 synthesis.

Patent application WO 00/42055 in the name of Zambon Group describes 3'-dedimethylamino-9-oxyimine macrolides possessing anti-inflammatory activity but without antibiotic activity.

Derivatives of azithromycin, without cladinose and desosamine, of formula

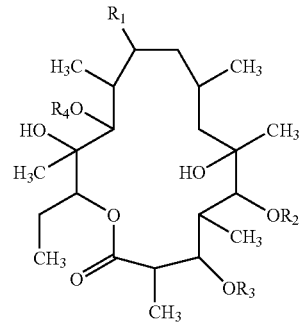

in which $R_1$ is a hydrogen atom, a lower alkyl or a lower alkanoyl; $R_2$, $R_3$ and $R_4$, which may be identical or different from one another, represent a hydrogen atom or a lower alkanoyl; they are described as anti-inflammatories in U.S. Pat. No. 4,886,792 (Sour Pliva); moreover, the same patent also claims intermediates in the synthesis of the aforementioned compounds in which $R_2$ is desosamine, $R_3$ and $R_4$ are a hydrogen atom and $R_1$ has the meanings already stated.

The use of erythromycin as anti-inflammatory that acts by reducing the release of interleukin 1 through inhibition of the mammalian glycoprotein mdr-P is claimed in patent application WO 92/16226 in the name of Smith-Kline Beecham Corporation.

The use of azithromycin for the treatment of noninfective inflammatory pathologies is claimed in the already cited patent application HR20010301 in the name of Pliva.

Besides, treatment other than acute treatment with substances that possess proven antimicrobial activity is highly undesirable because, as already mentioned, this would cause the rapid development of resistant strains and, in consequence, the thwarting of a valid antibiotic therapy.

Now we have found, surprisingly, that by removing the cladinose in position 3 from 9a-azalides, compounds are obtained that possess potent anti-inflammatory activity and are substantially devoid of antibiotic properties.

Therefore the present invention relates to the compounds of formula (I)

[chemical structure]

in which

R is a hydrogen atom or a methyl $R_1$ is a hydrogen atom, an N,N-di-$(C_1$-$C_3)$-alkylamino group, an N,N-di-$(C_1$-$C_3)$-alkylamino-N-oxide group, an N—$(C_1$-$C_4)$-acyl-N—$(C_1$-$C_3)$-alkylamino group or together with $R_2$ forms a bond between the carbon atoms at 3' and 4';

$R_2$ is a hydrogen atom or together with $R_1$ forms a bond between the carbon atoms at 3' and 4';

$R_3$ is a linear or branched $C_1$-$C_5$ alkyl, a benzyl optionally substituted with one or two substituents selected from nitro, hydroxy, carboxy, amino, linear or branched $C_1$-$C_5$ alkyl, $C_1$-$C_4$ alkoxy groups, $C_1$-$C_4$ alkoxycarbonyl groups, aminocarbonyl or cyano groups or a chain of formula —$(CH_2)r$-X—$(CH_2)m$-Y—$(CH_2)n$-A in which A is a hydrogen atom, a phenyl or an heteroaryl with five or six members containing from one to three atoms selected from nitrogen, oxygen and sulfur;

X represents O, S, SO, $SO_2$, $NR_6$ and $R_6$ is a hydrogen atom, a linear or branched $C_1$-$C_3$ alkyl, a $C_1$-$C_3$ alkoxycarbonyl group, a benzyloxycarbonyl group;

Y is a $C_6H_4$ group, a heteroaryl with five or six members containing from one to three atoms selected from nitrogen, oxygen and sulfur or represents O, S, SO, $SO_2$, $NR_6$ where $R_6$ has the meanings given above;

r is an integer of from 1 to 3;

m is an integer of from 1 to 6;

n is an integer of from 0 to 2;

moreover the nitrogen atom to which $R_3$ is bound can be present in the N-oxide form;

and their pharmaceutically acceptable salts;

provided that when R is a hydrogen atom and $R_1$ is a dimethylamino group, $R_3$ is different from a $(C_1$-$C_5)$-alkyl group.

The compounds of formula I in which R is a hydrogen atom, $R_1$ is a dimethylamino group and $R_3$ is a lower alkyl are described as synthesis intermediates in U.S. Pat. No. 4,886,792 (column 3, compound of formula V) in the name of Sour Pliva.

The compounds of formula I are anti-inflammatory macrolides that are devoid of antibiotic activity and can therefore be used in the treatment and prophylaxis of inflammatory pathologies.

The term linear or branched $C_1$-$C_5$ alkyl means a group selected from methyl, ethyl, n-propyl, isopropyl, n-butyl, isobutyl, sec-butyl, tert-butyl, n-pentyl and isopentyl.

The term heteroaryl with 5 or 6 members containing from 1 to 3 hetero atoms selected from nitrogen, oxygen and sulfur means heterocycles such as pyrrole, thiophene, furan, imidazole, pyrazole, thiazole, isothiazole, isoxazole, oxazole, pyridine, pyrazine, pyrimidine, pyridazine, triazole, thiadiazole.

It will be obvious to a person skilled in the art that substitution with partially or completely saturated forms of the heteroaryls as well as the presence of substituents on the aromatic rings (phenyl or heteroaryls) envisaged in the meanings of A and Y give rise to compounds that do not depart from the spirit of the invention.

Preferred compounds of formula I are those in which R, $R_2$ and $R_3$ have the meanings already stated and $R_1$ is a hydrogen atom, an N-methyl-N—$(C_1$-$C_3)$-alkylamino group, an N-methyl-N—$(C_1$-$C_3)$-alkylamino-N-oxide group, an N—$(C_1$-$C_4)$-acyl-N-methylamino group or $R_1$ together with $R_2$ forms a bond between the carbon atoms at 3' and 4'.

Belonging to this group, and even more preferred, are the compounds of formula I in which $R_1$ is a hydrogen atom, an N,N-dimethylamino group, an N,N-dimethylamino-N-oxide group, an N-acetyl-N-methylamino group or $R_1$ together with $R_2$ forms a bond between the carbon atoms at 3' and 4'.

Among the compounds of formula I in which R, $R_1$ and $R_2$ have the meanings already stated, those are preferred in which $R_3$ is a linear or branched $(C_1$-$C_3)$ alkyl, a benzyl optionally substituted with one or two substituents selected from nitro, hydroxy, carboxy, amino, linear or branched $(C_1$-$C_3)$ alkyl, $C_1$-$C_4$ alkoxy and cyano groups or a chain with the formula —$(CH_2)r$-X—$(CH_2)m$-Y—$(CH_2)n$-A in which A is a hydrogen atom, a phenyl or a heteroaryl with five or six members containing from one to three atoms selected from nitrogen, oxygen and sulfur;

X is O or $NR_6$ and $R_6$ is a hydrogen atom, a linear or branched $C_1$-$C_3$ alkyl;

Y, when n is 0, is a $C_6H_4$ group or a heteroaryl with five or six members containing from one to three atoms selected from nitrogen, oxygen and sulfur; or, when n is not 0, it is O or $NR_6$ and $R_6$ is a hydrogen atom, a linear or branched $C_1$-$C_3$ alkyl;

r is an integer of from 1 to 3;

m is an integer selected from 1 and 2;

n is an integer of from 0 to 2;

moreover the nitrogen atom to which $R_3$ is bound can be present in the N-oxide form;

Within the scope of this group of compounds of formula 1, those are preferred in which $R_3$ is a methyl, a benzyl or a chain with the formula

—(CH$_2$)$r$-X—(CH$_2$)$m$-Y—(CH$_2$)$n$-A in which

A is a hydrogen atom, a phenyl or a heteroaryl with five or six members selected from pyrrole, thiophene, furan, imidazole, oxazole, thiazole, pyridine, pyrimidine, triazole and thiadiazole;

X is O or $NR_6$ and $R_6$ is a hydrogen atom;

Y, when n is 0, is a $C_6H_4$ group or a heteroaryl with five or six members selected from pyrrole, thiophene, furan, imidazole, oxazole, thiazole, pyridine, pyrimidine, triazole and thiadiazole; or, when n is 1, it is $NR_6$ and $R_6$ is a hydrogen atom;

r is an integer of from 1 to 3;

m is an integer selected from 1 and 2;

n is an integer selected from 0 and 1;

moreover the nitrogen atom to which $R_3$ is bound can be present in the N-oxide form;

Belonging to this group, and even more preferred, are the compounds of formula I in which $R_3$ is a methyl, a benzyl or a chain with the formula

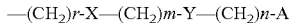
—(CH$_2$)$r$-X—(CH$_2$)$m$-Y—(CH$_2$)$n$-A in which

A is a hydrogen atom, a phenyl or a heteroaryl selected from thiophene, furan, imidazole, thiazole, pyridine and triazole;

X is $NR_6$ and $R_6$ is a hydrogen atom;

Y, when n is 0, is a $C_6H_4$ group or a heteroaryl selected from thiophene, furan, imidazole, thiazole, pyridine and triazole; or, when n is 1, it is $NR_6$ and $R_6$ is a hydrogen atom;

r is 3;

m is an integer selected from 1 and 2;

n is an integer selected from 0 and 1;

moreover the nitrogen atom to which $R_3$ is bound can be present in the N-oxide form;

Moreover, compounds of formula I are preferred in which R and $R_2$ have the meanings already stated, $R_1$ is a hydrogen atom, an N-methyl-N-($C_1$-$C_3$)-alkylamino group, an N-methyl-N-($C_1$-$C_3$)-alkylamino-N-oxide group, an N-($C_1$-$C_4$)-acyl-N-methylamino group or $R_1$ together with $R_2$ forms a bond between the carbon atoms at 3' and 4'; at the same time $R_3$ is a linear or branched ($C_1$-$C_3$) alkyl, a benzyl optionally substituted with one or two substituents selected from nitro, hydroxy, carboxy, amino, linear or branched ($C_1$-$C_3$) alkyl, $C_1$-$C_4$ alkoxy and cyano groups or a chain with the formula

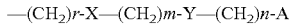
—(CH$_2$)$r$-X—(CH$_2$)$m$-Y—(CH$_2$)$n$-A in which

A is a hydrogen atom, a phenyl or a heteroaryl with five or six members containing from one to three atoms selected from nitrogen, oxygen and sulfur;

X is O or $NR_6$ and $R_6$ is a hydrogen atom, a linear or branched $C_1$-$C_3$ alkyl;

Y, when n is 0, is a $C_6H_4$ group or a heteroaryl with five or six members containing from one to three atoms selected from nitrogen, oxygen and sulfur; or, when n is different from 0, it is O or $NR_6$ and $R_6$ is a hydrogen atom, a linear or branched $C_1$-$C_3$ alkyl;

r is an integer of from 1 to 3;

m is an integer selected from 1 and 2;

n is an integer of from 0 to 2;

moreover the nitrogen atom to which $R_3$ is bound can be present in the N-oxide form;

Within the scope of this group of compounds of formula I, those are preferred in which $R_3$ is a methyl, a benzyl or a chain with the formula

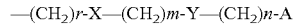
—(CH$_2$)$r$-X—(CH$_2$)$m$-Y—(CH$_2$)$n$-A in which

A is a hydrogen atom, a phenyl or a heteroaryl with five or six members selected from pyrrole, thiophene, furan, imidazole, oxazole, thiazole, pyridine, pyrimidine, triazole and thiadiazole;

X is O or $NR_6$ and $R_6$ is a hydrogen atom;

Y, when n is 0, is a $C_6H_4$ group or a heteroaryl with five or six members selected from pyrrole, thiophene, furan, imidazole, oxazole, thiazole, pyridine, pyrimidine, triazole and thiadiazole; or, when n is 1, it is $NR_6$ and $R_6$ is a hydrogen atom;

r is an integer of from 1 to 3;

m is an integer selected from 1 and 2;

n is an integer selected from 0 and 1;

moreover the nitrogen atom to which $R_3$ is bound can be present in the N-oxide form;

Belonging to this group, and even more preferred, are the compounds of formula I in which $R_3$ is a methyl, a benzyl or a chain with the formula

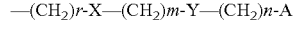
—(CH$_2$)$r$-X—(CH$_2$)$m$-Y—(CH$_2$)$n$-A in which

A is a hydrogen atom, a phenyl or a heteroaryl selected from thiophene, furan, imidazole, thiazole, pyridine and triazole;

X is $NR_6$ and $R_6$ is a hydrogen atom;

Y, when n is 0, is a $C_6H_4$ group or a heteroaryl selected from thiophene, furan, imidazole, thiazole, pyridine and triazole; or, when n is 1, it is $NR_6$ and $R_6$ is a hydrogen atom;

r is 3;

m is an integer selected from 1 and 2;

n is an integer selected from 0 and 1;

moreover the nitrogen atom to which $R_3$ is bound can be present in the N-oxide form;

Belonging to this last-mentioned group, and even more preferred, are the compounds of formula I in which $R_1$ is a hydrogen atom, an N,N-dimethylamino group, an N,N-dimethylamino-N-oxide group, an N-acetyl-N-methylamino group or $R_1$ together with $R_2$ forms a bond between the carbon atoms at 3' and 4'.

Examples of pharmaceutically acceptable salts of the compounds of formula I are salts with organic or inorganic acids such as hydrochloric, hydrobromic, hydroiodic, nitric, sulfuric, phosphoric, acetic, tartaric, citric, benzoic, succinic and glutaric acid.

Specific examples of compounds covered by the present invention are those in which R and $R_2$ have the meanings given in formula I and $R_1$ together with $R_2$ forms a bond between the carbon atoms at 3' and 4' or $R_1$ is a hydrogen atom, an N,N-dimethylamino group, an N,N-dimethylamino-N-oxide group or an N-acetyl-N-methylamino group and at the same time $R_3$ is a methyl, a benzyl, a 3-[(thiazol-2-yl-methyl)-amino]-propyl, 3-[(thiophen-2-yl-methyl)-amino]-propyl, 3-[(furan-2-yl-methyl)-amino]-propyl, 3-[(imidazol-2-yl-methyl)-amino]-propyl, 3-(benzylamino)-propyl, 3-[2-

[(thiazol-2-yl-methyl)-amino]-ethylamino]-propyl,3-[6 (benzylamino)-hexylamino]-propyl group; moreover, the nitrogen atom to which R₃ is bound can be present in the N-oxide form.

The compounds of formula I that are covered by the present invention are prepared following a synthetic scheme that comprises removal of the L-cladinose at position 3 from the compounds of formula

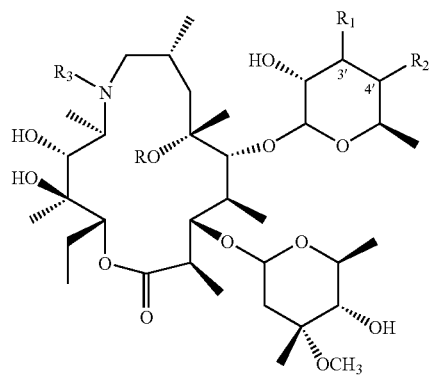

(II)

in which

R, R₁, R₂ and R₃ have the meanings given for the compounds of formula I.

Removal of cladinose is preferably effected through a catalyzed reaction of acid hydrolysis in the presence of an inorganic acid such as sulfuric acid or hydrochloric acid or of a protic organic solvent such as water, methanol or ethanol.

The compounds of formula II are obtained from erythromycin A oxime by Beckmann rearrangement, reduction to amine and then functionalization of the latter; any synthetic interventions at the level of the dimethylamino group at position 3' comprise N-oxidation, complete removal or demethylation and subsequent functionalization (alkylation and acylation).

For the synthesis of the compounds of formula I in which the substituent R is methyl, the synthetic scheme is similar but starting from 6-O-methylerythromycin A oxime or, alternatively, the azalide of interest is methylated in accordance with known techniques.

It will be obvious to a person skilled in the art that in order to avoid interference with any functional groups present at positions where structural modifications are to be made, it will be more or less suitable and appropriate to choose a particular priority in the synthetic interventions to be carried out.

For example, any intervention on the dimethylamino group at position 3' can follow or precede the procedure for enlargement of the macrolide ring or can constitute the concluding step of the said synthesis.

As a further example, considering removal of the cladinose, this is effected subsequently to the reactions that lead to enlargement of the macrolide ring and can follow or precede any structural modifications at position 3'.

As a rule, however, there are no interactions that prevent the cladinose being removed in some other intermediate step or at the end of the synthetic process.

These choices of procedure will be dictated, at times, by technical requirements with the objective of optimizing the synthetic process of the product of interest.

The instructions for carrying out the aforementioned structural modifications on the macrolides are described better hereunder.

The oximes of erythromycin A, with Z or E configuration, are known compounds that are available commercially and can be prepared by conventional techniques, for example those cited in U.S. Pat. No. 3,478,014 in the name of Pliva or those described in the literature (J. C. Gasc et al.: The Journal of Antibiotics; 44, 313-330, 1991).

The synthesis of 9-deoxo-9a-aza-9a-homoerythromycin A is carried out according to conventional techniques, for example Beckmann rearrangement and successive reduction to amine of erythromycin A oxime (U.S. Pat. No. 4,328,334 Pliva Pharm. & Chem. Works) (Djokic S. et al., J. Chem. Soc. Perkin Trans., 1986, 1881) to give the compounds of formula

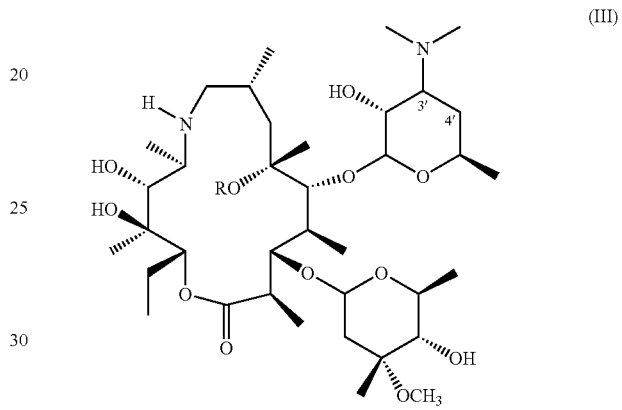

(III)

in which

R has the meanings given in formula 1.

Substitution of the aza lactone thus obtained is effected via a reaction of addition onto activated olefins to obtain the corresponding 9a-amino-, hydroxy- or mercapto-alkyl derivatives then functionalized at the heteroatom following conventional synthetic techniques; or, to obtain N-alkyl derivatives, possibly substituted, a reducing alkylation reaction is used via a reaction with aldehydes in the presence of a reducing agent.

Both methods lead to compounds of formula

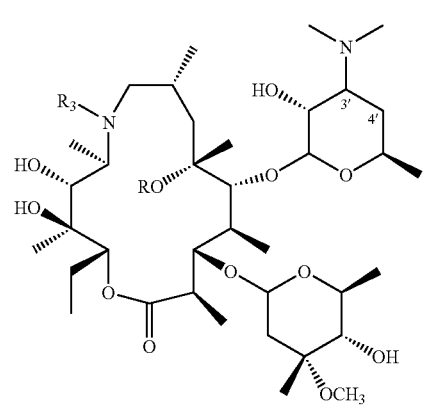

(IV)

in which

R and R₃ have the meanings given in formula I.

Methylation of the 9a amino group according to the Eschweiler-Clark reaction with formaldehyde in the presence of formic acid is described in patent BE 892,357 (Pliva Pharm. & Chem. Works).

U.S. Pat. No. 4,464,527 (Pfizer Inc.) describes the process for obtaining the N-ethyl and the N-(n-propyl) derivative of 9-deoxo-9a-aza-9a-homoerythromycin A.

Conversion to the corresponding N-oxides is effected, according to known methods, by treatment with peracids, e.g. hydrogen peroxide or metachloroperbenzoic acid in the presence of an organic solvent (U.S. Pat. No. 3,928,387, Hoffmann-La Roche Inc., already cited) (J. Am. Chem. Soc. 1954, 76, 3121).

Removal of the dimethylamino group is effected, according to known methods, by oxidation, pyrolysis and if necessary reduction of the 9a-derivatives of azithromycin of formula IV.

It will be obvious to a person skilled in the art that in order to avoid interference with any functional groups that are present on substituent $R_3$, removal of the dimethylamino group will preferably be carried out starting from intermediates of formula

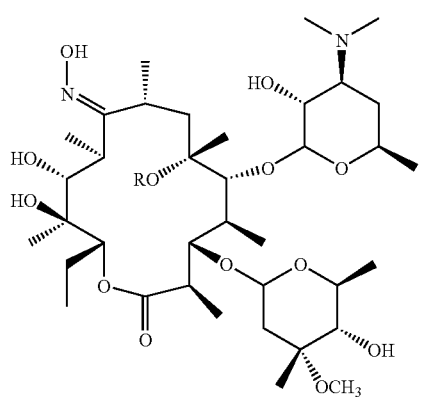

(V)

in which

R has the meanings already stated.

Oxidation gives the N-oxide compounds of formula

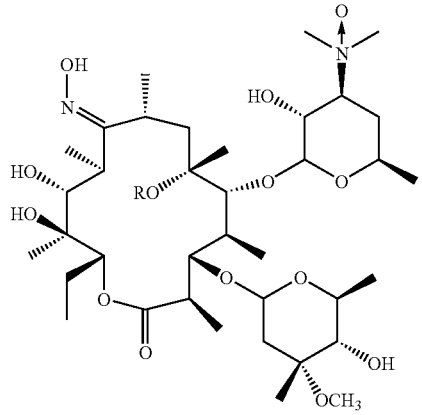

(VI)

in which

R has the meanings already stated;

by pyrolysis, followed if necessary by reduction, these give respectively the compounds of formula VIIIa and VIIb

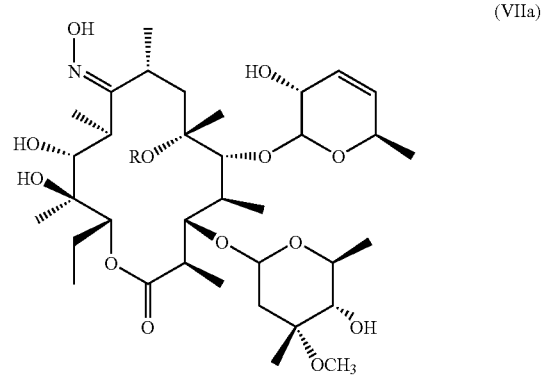

(VIIa)

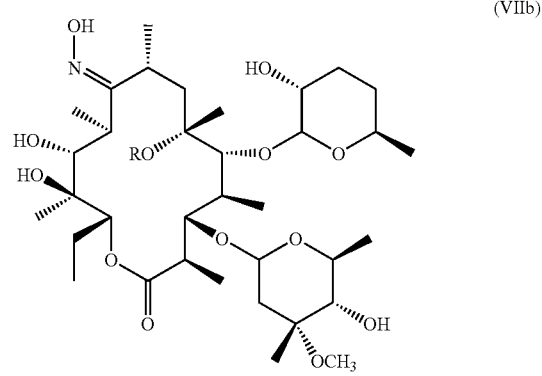

(VIIb)

in which

R has the meanings already stated;

which are converted to the corresponding compounds of formula II in which R, $R_2$ and $R_3$ have the meanings already stated and $R_1$ is a hydrogen atom or together with $R_2$ forms a bond between the carbon atoms at 3' and 4' by Beckmann rearrangement and reduction to amine of the oxime at position 9 and subsequent functionalization of the 9a-azalide thus obtained as described previously.

The mono-demethylation of the dimethylamino group at position 3' is carried out, using conventional techniques, by treatment with benzyl chloroformate in the presence of an excess of base, for example alkaline hydrogen carbonate, and of an inert solvent followed by elimination of the benzyloxycarbonyl group at position 2' and 3' as described in U.S. Pat. No. 5,250,518 in the name of Pliva; the subsequent reactions of acylation or alkylation of the secondary amine thus obtained are carried out in accordance with conventional synthetic techniques.

Moreover, the compounds of formula I in which $R_1=R_2=H$ can be prepared by reduction of the corresponding compounds of formula I in which $R_1$ and $R_2$ together form a bond.

The process described above, in one of its embodiments, envisages using, as substrate, the compound of formula II in which R is methyl, $R_1$ is a dimethylamino group, $R_2$ is a hydrogen atom and $R_3$ is methyl (azithromycin) and consists of carrying out the synthetic intervention on the dimethylamino group at position 3' and removal of the L-cladinose following the techniques described previously.

As noted above, the compounds of formula I to which the present invention relates are endowed with anti-inflammatory activity but are devoid of antibiotic activity.

The pharmacological activity of the compounds of formula I has been evaluated in models of cutaneous and pulmonary inflammation in comparison with known macrolides, such as erythromycin and azithromycin, which have both anti-inflammatory and antibiotic activity.

The anti-inflammatory activity was evaluated in vivo both as inhibition of mouse ear edema induced by PMA (phorbol myristate acetate) and as reduction of the accumulation of neutrophils in the rat lung induced by LPS (E. coli lipopolysaccharide).

In all the tests, the compounds of the present invention were found to be very active as anti-inflammatories and the anti-inflammatory activity was found to be comparable or greater than that of the comparative compounds.

Furthermore, the compounds of the present invention do not exhibit antibiotic activity, as was demonstrated by the tests that were carried out, and therefore can be used in long-term treatments of inflammatory processes without the development of undesirable phenomena of resistance.

It is therefore clear that the compounds of formula I, which have anti-inflammatory activity but are devoid of antibiotic activity, can be useful in both acute and chronic treatment and in the prophylaxis of inflammatory pathologies, especially of those pathologies associated with altered cellular functionality of the neutrophils, for example rheumatoid arthritis, vasculitis, glomerulonephritis, damage from ischemic reperfusion, atherosclerosis, septic shock, ARDS, COPD and asthma.

The therapeutically effective quantities will depend on the age and on the general physiological condition of the patient, the route of administration and the pharmaceutical formulation used; the therapeutic doses will generally be between about 10 and 2000 mg/day and preferably between about 30 and 1500 mg/day.

The compounds of the present invention for use in treatment and/or prophylaxis of the pathologies indicated above will preferably be used in a pharmaceutical form suitable for oral, rectal, sublingual, parenteral, topical, transdermal and inhalational administration.

The present invention further relates to pharmaceutical formulations containing a therapeutically effective quantity of a compound of formula I or of one of its salts mixed with a pharmaceutically acceptable vehicle. The pharmaceutical formulations of the present invention can be liquids that are suitable for oral and/or parenteral administration, for example, drops, syrups, solutions, injectable solutions that are ready for use or are prepared by the dilution of a freeze-dried product but are preferably solid or semisolid as tablets, capsules, granules, powders, pellets, pessaries, suppositories, creams, salves, gels, ointments; or solutions, suspensions, emulsions, or other forms suitable for administration by the transdermal route or by inhalation.

Depending on the type of formulation, in addition to a therapeutically effective quantity of one or more compounds of formula I, they will contain solid or liquid excipients or diluents for pharmaceutical use and possibly other additives normally used in the preparation of pharmaceutical formulations, such as thickeners, aggregating agents, lubricants, disintegrating agents, flavorings and colorants.

The pharmaceutical formulations of the invention can be produced in accordance with the usual methods.

The following examples are provided for better illustrating the present invention.

The table that precedes the examples gives the chemical structures and analytical characterization of the synthetic intermediates and of the compounds of formula I.

| | | |
|---|---|---|
| intermediate 4 | 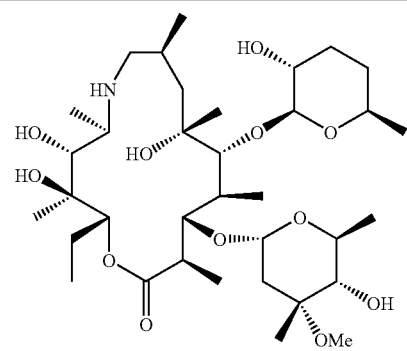 | CDCl$_3$: 5.04(d, 1H, J=4.2, H$_1$"); 4.73-4.78(m, 1H, H$_{13}$); 4.35(d, 1H, J=7.1, H$_1$'); 4.28(m, 1H, H$_5$); 3.64(d, J=6.6, H$_{11}$); 3.40(s, 3H, H$_7$"). |
| intermediate 5 | 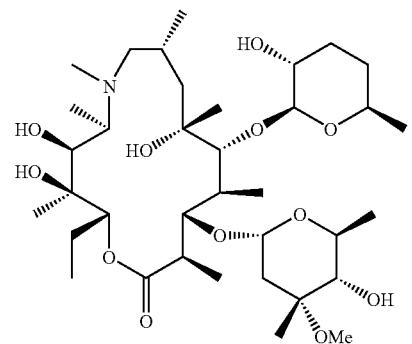 | CDCl$_3$: 5.10(d, 1H, J=4.3, H$_1$"); 4.67-4.72 (m, 1H, H$_{13}$); 4.36(d, 1H, J=7.6, H$_1$'); 4.25(m, 1H, H$_3$); 4.12(m, 1H, H$_5$); 3.35(s, 3H, H$_7$"); 2.35(s, 3H, NCH$_3$). |

| | | |
|---|---|---|
| intermediate 14 | 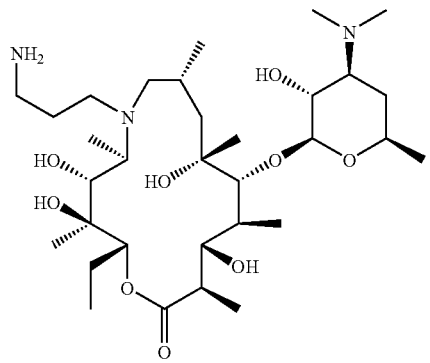 | DMSO_d6: 5.0-5.1(m, 1H, H$_{13}$); 4.58(d, 1H, J=7.4, H$_1$'); 0.77(t, 3H, J=7.0, H$_{15}$). |
| compound 6 | 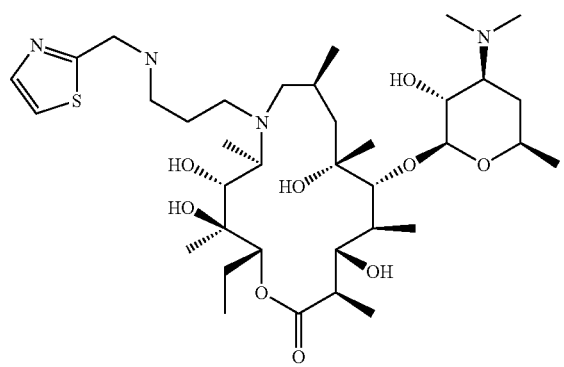 | CDCl$_3$: 7.74(m, 1H, Th); 7.28(m, 1H, Th); 5.0-5.2(m, 1H, H$_{13}$); 4.50(d, 1H, J=7.3, H$_1$'); 4.23 (m, 2H, Th—CH$_2$); 2.34(s, 6H, Me$_2$N); 0.89(t, 3H, J=7.3, H$_{15}$). |
| compound 10 | 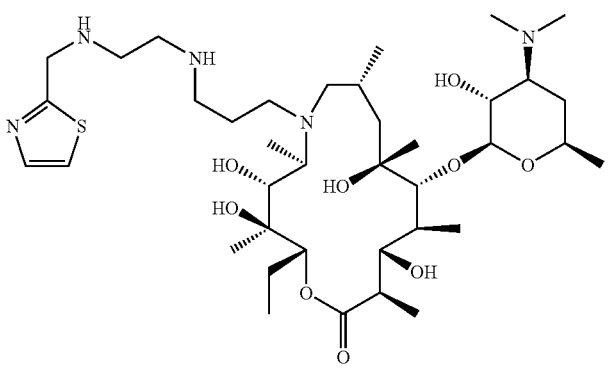 | CDCl$_3$: 7.72(m, 1H, Th); 7.28(m, 1H, Th); 5.01-5.06(m, 1H, H$_{13}$); 4.44(d, 1H, J=7.3, H$_1$'); 4.18(m, 2H, Th—CH$_2$); 2.27(s, 6H, Me$_2$N); 0.83(t, 3H, J=7.3, H$_{15}$). |
| compound 9 | 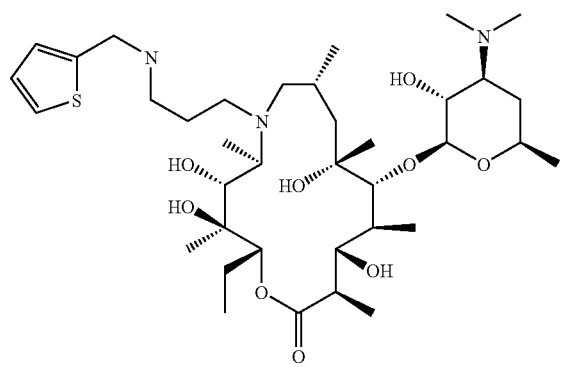 | CDCl$_3$: 7.23, 7.03 and 6.97(3m, 3H, Tiophenyl); 5.13(m, 1H, H$_{13}$); 4.46(d, 1H, J=7.3, H$_1$'); 4.06(m, 2H, T—CH$_2$); 2.29(s, 6H, Me$_2$N); 0.90(t, 3H, J=7.4, H$_{15}$). |

-continued
| | | |
|---|---|---|
| compound 7 | 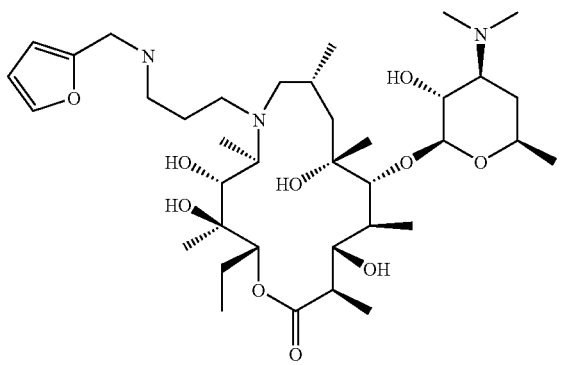 | CDCl$_3$: 7.36(m, 1H, Furyl), 6.28-6.31(2m, 2H, Furyl); 5.05-5.10(m, 1H, H$_{13}$); 4.45(d, 1H, J=7.3, H$_1$'); 3.87(m, 2H, F—CH$_2$); 2.28(s, 6H, Me$_2$N); 0.89(t, 3H, J=7.4, H$_{15}$). |
| compound 8 | 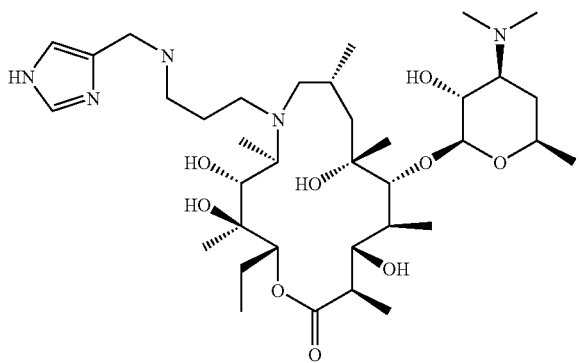 | CDCl$_3$: 7.58(m, 1H, N=CH—N Imidazol), 6.97(s, 1H, N—CH=C imidazol); 5.10-5.16(m, 1H, H$_{13}$); 4.44(d, 1H, J=7.4, H$_1$'); 2.28(s, 6H, Me$_2$N); 0.91(t, 3H, J=7.4, H$_{15}$). |
| intermediate 1 | 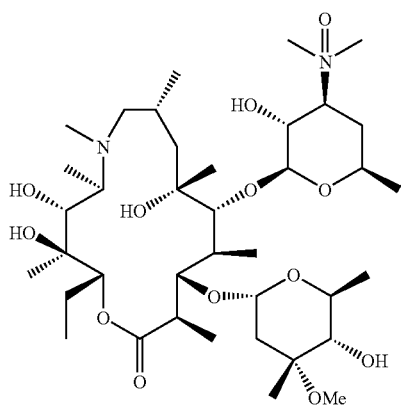 | CDCl$_3$: 5.18(d, J=4.6, 1H, H$_1$'); 4.69(m, 1H, H$_{13}$); 4.56(d, 1H, J=7.0, H$_1$'); 4.28(m, 1H, H$_3$); 3.40 and 3.21(2s, 6H, Me$_2$N[O]); 2.33(s, 3H, NCH$_3$). |
| compound 11 | 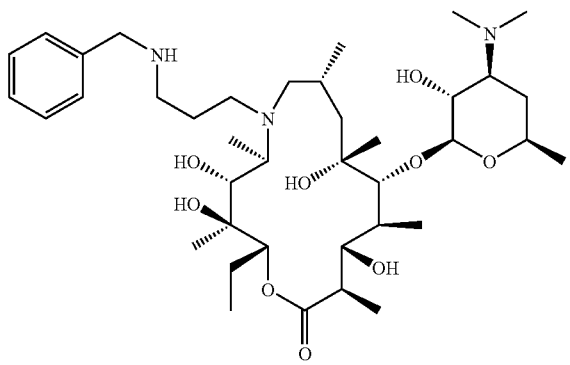 | D$_2$O: 7.38(m, 5H, Ph); 4.9-5.0(m, 1H, H$_{13}$); 4.14(s, 2H, CH$_2$Ph); 2.73(s, 6H. Me$_2$N); 0.73(t, 3H, J=7.1, H$_{15}$). |

| | | |
|---|---|---|
| compound 12 | 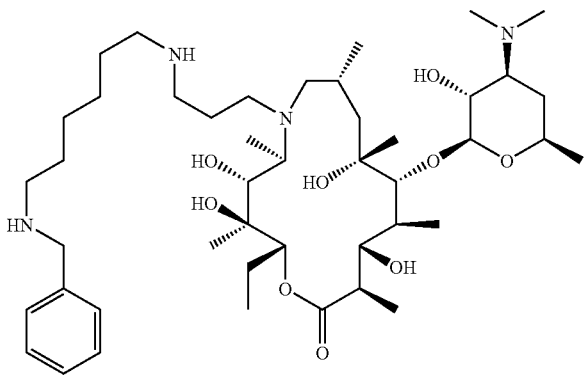 | DMSO_d$_6$: 7.2-7.35(m, 5H, Phenyl); 5.00-5.06(m, 1H, H$_{13}$); 4.46(d, 1H, J=7.4, H$_1$'); 3.67(m, 2H, Ph—CH$_2$); 2.21(s, 6H, Me$_2$N); 0.75(t, 3H, J=7.0, H$_{15}$). |
| intermediate 20 | 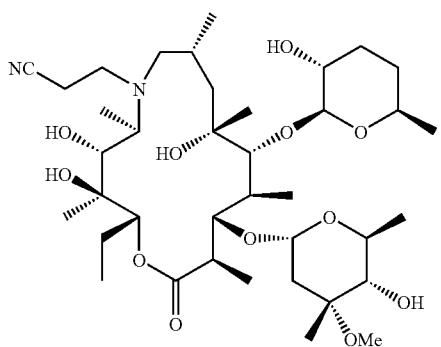 | CDCl$_3$: 4.92(d, 1H, J=4.4, H$_1$"); 4.75-4.80(m, 1H, H$_{13}$); 4.39(d, 1H, J=7.5, H$_1$'); 3.31(s, 3H, H$_7$"); 0.93(t, 3H, J=7.5, H$_{15}$). |
| intermediate 21 | 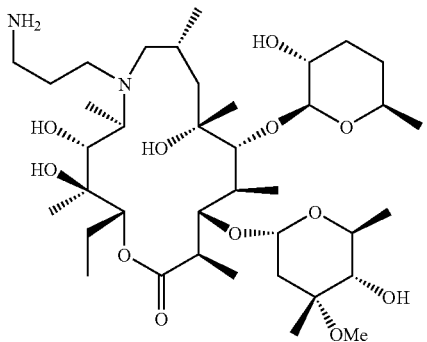 | CDCl$_3$: 5.09(d, 1H, J=4.5, H$_1$"); 4.91-4.96(m, 1H, H$_{13}$); 4.38(d, 1H, J=7.5, H$_1$'); 3.33(s, 3H, H$_7$"); 0.88(t, 3H, J=7.3, H$_{15}$). |
| intermediate 24 | 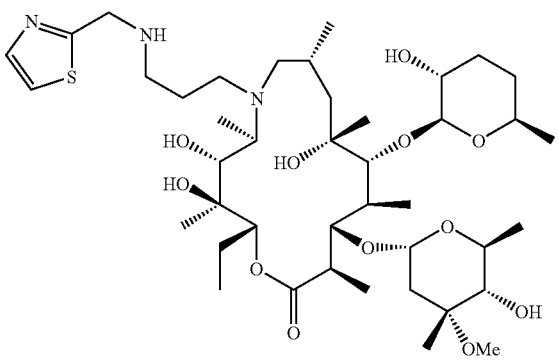 | CDCl$_3$: 7.74(m, 1H, Th); 7.30(m, 1H, Th); 5.10(d, 1H, J=4.3, H$_1$"); 5.01(m, 1H, H$_{13}$); 4.40(d, 1H, J=7.6, H$_1$'); 4.21(m, 2H, Th—CH$_2$); 3.69(s, 1H, H$_{11}$); 3.34(s, 3H, H$_7$"); 0.90(t, 3H, J=7.4, H$_{15}$). |

-continued
| | | |
|---|---|---|
| compound 14 | 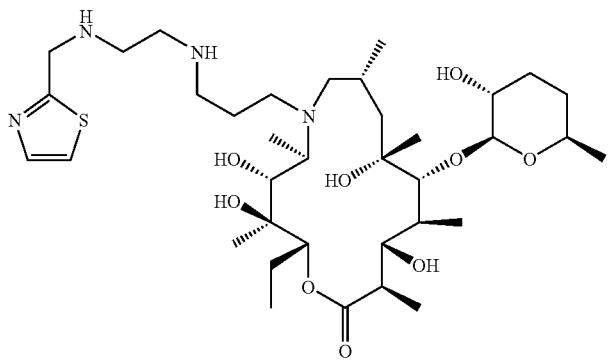 | CDCl$_3$: 7.73(m, 1H, Th); 7.28(m, 1H, Th); 5.0-5.1(m, 1H, H$_{13}$); 4.37(d, 1H, J=7.9, H$_1$'); 4.20 (m, 2H, Th—CH$_2$); 0.87(t, 3H, J=7.5, H$_{15}$). |
| intermediate 23 | 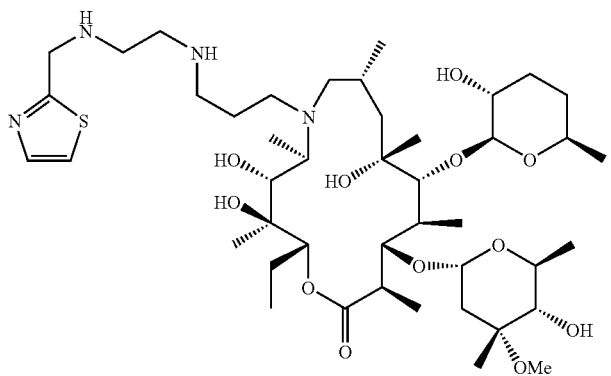 | CDCl$_3$: 7.71(m, 1H, Th); 7.26(m, 1H, Th); 5.08(d, 1H, J=4.2, H$_1$''); 4.86-4.94(m, 1H, H$_{13}$); 4.39(d, 1H, J=7.6, H$_1$'); 4.18(m, 2H, Th—CH$_2$); 3.32(s, 3H, H$_7$''); 0.82(t, 3H, J=7.3, H$_{15}$). |
| compound 13 | 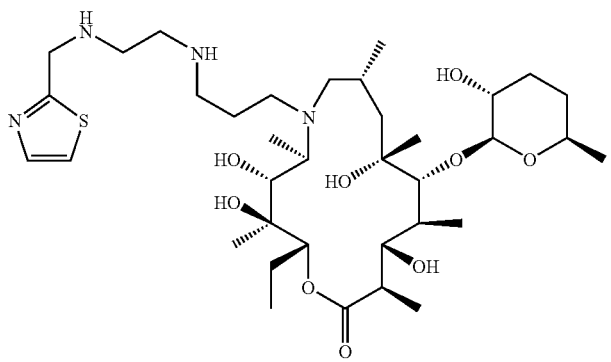 | CDCl$_3$: 7.73(m, 1H, Th); 7.28(m, 1H, Th); 4.96-5.03(m, 1H, H$_{13}$); 4.35(d, 1H, J=7.6, H$_1$'); 4.20(m, 2H, Th—CH$_2$); 0.83(t, 3H, J=7.6, H$_{15}$). |
| intermediate 6 | 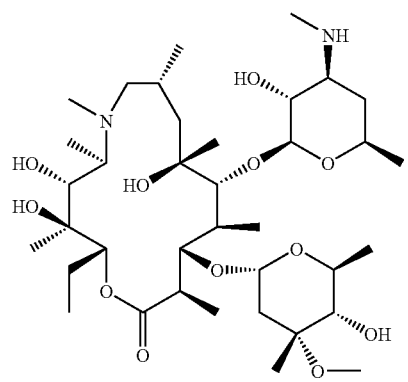 | DMSO_d6: 4.8(m, 2H, H$_{13}$ and H$_1$''); 4.43(d, 1H, J=7.1, H$_1$'); 0.79(t, 3H, J=7.3, H$_{15}$). |

-continued
| | | |
|---|---|---|
| compound 1 | 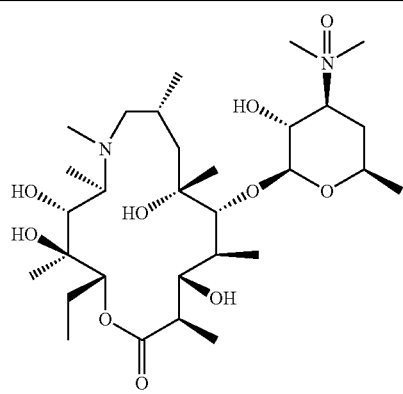 | CDCl₃: 4.75-4.69(m, 1H, H₁₃); 4.61(d, 1H, J=7.1, H₁'); 3.61(s, 1H, H₁₁); 3.19 and 3.16(2s, 6H, Me₂N[O]); 2.38(s, 3H, CH₃N). |
| compound 2 | 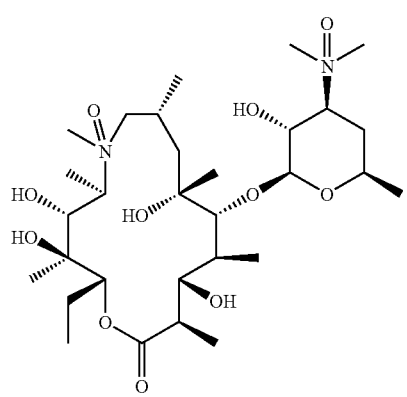 | CDCl₃: 5.38-5.43(m, 1H, H₁₃); 4.48(d, 1H, J=7.0, H₁'); 3.30 and 3.16(2s, 6H, Me₂N[O]); 2.93(s, 3H, MeN[O]); 0.90(t, 3H, J=6.5, H₁₅). |
| intermediate 3 | 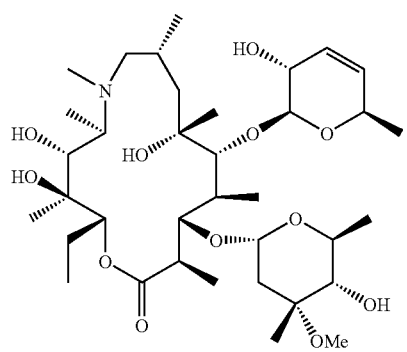 | CDCl₃: 5.67(m, 2H, CH₃'=CH₄'); 4.99(d, 1H, J=4.4, H₁''); 4.66-4.70(m, 1H, H₁₃); 4.54(d, 1H, J=6.5, H₁'); 3.30(s, 3H, H₇''); 2.37(s, 3H, CH₃N). |
| compound 3 | 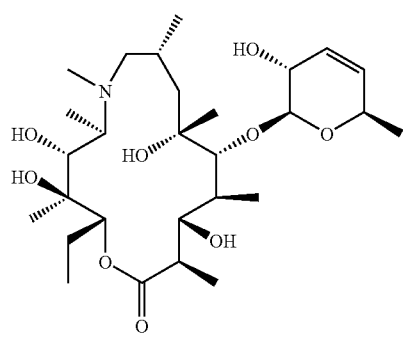 | CDCl₃: 5.66(m, 2H, CH₃'=CH₄'); 4.69-4.74 (m, 1H, H₁₃); 4.60(d, 1H, J=6.9, H₁'); 3.61(s, 1H, H₁₁); 2.66(s, 3H, CH₃N). |

-continued
| | | |
|---|---|---|
| compound 4 | 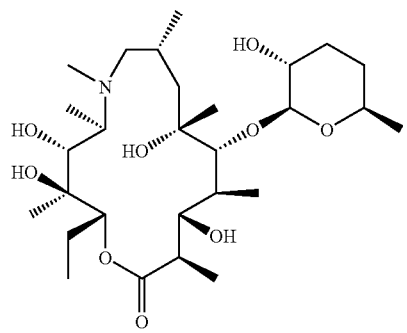 | CDCl$_3$: 4.67-4.75(m, 1H, H$_{13}$); 4.39(d, 1H, J=7.6, H$_1$'); 3.61(s, 1H, H$_{11}$); 2.38(s, 3H, CH$_3$N). |
| intermediate 7 | 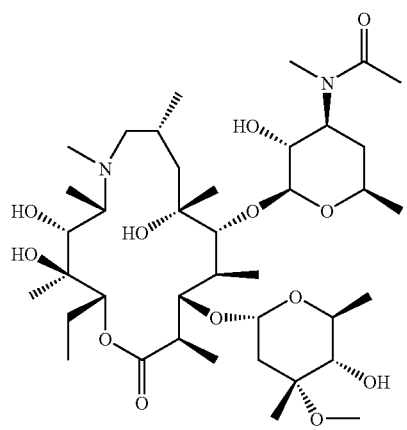 | CDCl$_3$: 5.08(m, 1H, H$_1$''); 4.6-4.8(m, 1H, H$_{13}$); 4.48-4.54(m, 1H, H$_1$'); 4.22(m, 1H, H$_3$); 3.39 and 3.34(2s, 3H, conformers H$_7$''); 2.93 and 2.86(2s, 3H, conformers CH$_3$N[CO]; 2.35(s, 3H, NCH$_3$) 2.19 and 2.14(2s, 3H, conformers N[CO]CH$_3$). |
| compound 5 | 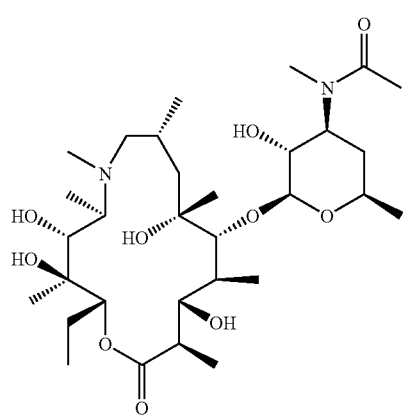 | CDCl$_3$: 4.96-5.05(m, 1H, H$_{13}$); 4.62(d, 1H, J=7.3, H$_1$'); 2.92, 2.85 and 2.83(3s, 6H, CH$_3$N and conformers CH$_3$N[CO]; 2.19 and 2.12(2s, 3H, conformers N[CO]CH$_3$). |
| intermediate 11 | 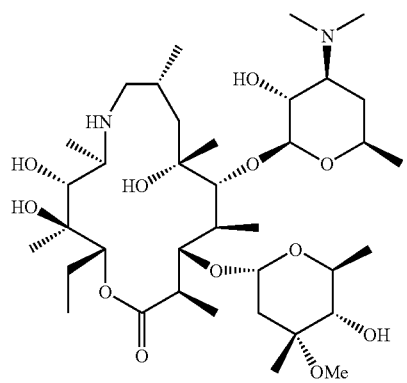 | CDCl$_3$: 5.05(m, 1H, H$_1$''); 4.70(m, 1H, H$_{13}$); 4.40(m, 1H, H$_1$'); 3.32(s, 3H, H$_7$''); 2.25(s, 6H, NMe$_2$); 0.85(m, 3H, H$_{15}$). |

-continued
| | | |
|---|---|---|
| intermediate 12 | 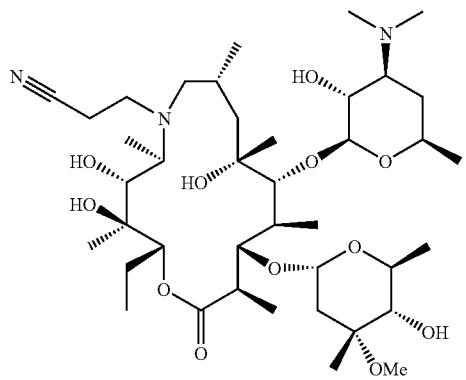 | CDCl₃: 4.98(m, 1H, H₁″); 4.63(m, 1H, H₁₃); 4.45(m, 1H, H₁′); 3.30(s, 3H, H₇″); 2.27(s, 6H, NMe₂); 0.89(m, 3H, H₁₅). |
| intermediate 13 | 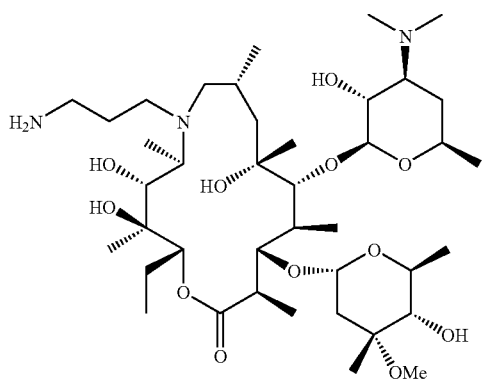 | CDCl₃: 5.03(m, 1H, H₁″); 4.87(m, 1H, H₁₃); 4.45(m, 1H, H₁′); 2.25(s, 6H, NMe₂); 0.81(m, 3H, H₁₅). |
| intermediate 17 | 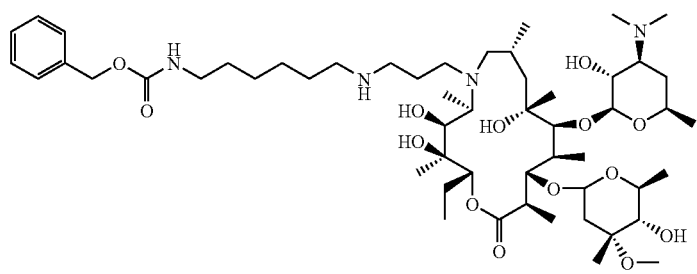 | CDCl₃: 7.3-7.4(m, 5H, Ph); 5.05-5.10(m, 3H, CH₂Ph + H₁″); 4.86(m, 1H, H₁₃); 4.45(m, 1H, H₁′); 3.30(s, 3H, H₇″); 2.27(s, 6H, NMe₂); 0.84 (m, 3H, H₁₅). |
| intermediate 16 | 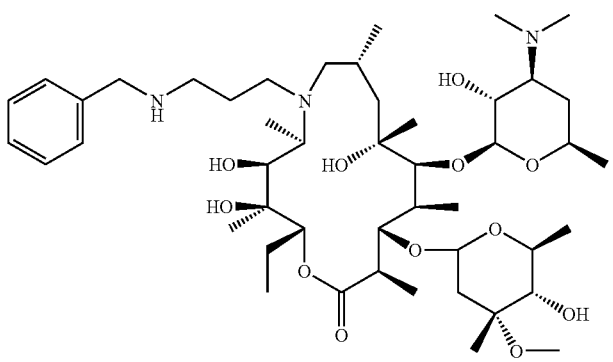 | CDCl₃: 7.2-7.4(m, 5H, Ph); 5.08(m, 3H, H₁″); 4.98(m, 1H, H₁₃); 4.47(m, 1H, H₁′); 3.30(s, 3H, H₇″); 2.34(s, 6H, NMe₂); 0.88(m, 3H, H₁₅). |

-continued

| intermediate 18 | 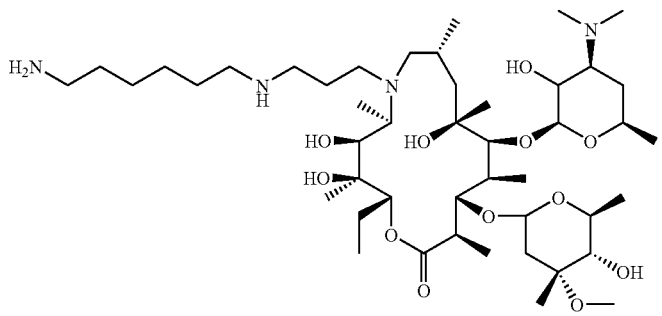 | CDCl$_3$: 5.03(m, 1H, H$_1$"); 4.84(m, 1H, H$_{13}$); 4.43(m, 1H, H$_1$'); 3.28(s, 3H, H$_7$"); 2.24(s, 6H, NMe$_2$); 0.88(m, 3H, H$_{15}$). |
|---|---|---|
| intermediate 19 | 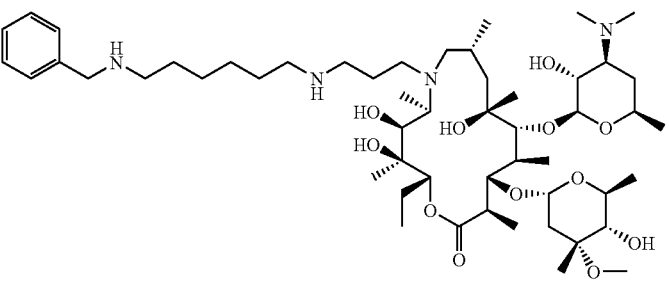 | CDCl$_3$: 7.2-7.3(m, 5H, Ph); 5.05(m, 3H, H$_1$"); 4.87(m, 1H, H$_{13}$); 4.45(m, 1H, H$_1$'); 3.75(m, 2H, CH$_2$Ph); 3.30(s, 3H, H$_7$"); 2.27(s, 6H, NMe$_2$); 0.83(m, 3H, H$_{15}$). |

EXAMPLE 1

Preparation of Intermediate 1

Metachloroperbenzoic acid (0.90 g, 4.1 mmol) was added in small portions to solution of azithromycin (3 g, 4 mmol) in chloroform (30 ml) and the mixture was stirred at room temperature for 4 h. The organic phase was diluted with CH$_2$Cl$_2$, washed with aqueous solutions at 10% of K$_2$CO$_3$, at 5% of NaCHO$_3$ and at 20% of NaCl, dehydrated with sodium sulfate, filtered and evaporated from the solvent under vacuum. The raw material was purified by Biotage chromatography (silica 40M cartridge, eluent CH$_2$Cl$_2$/MeOH/NH$_3$ 93/7/0.7) to give intermediate 1 (2.4 g, yield 78%) as a white solid and intermediate 2 as by-product (223 mg, yield 8%).

[M+I]$^+$ 766

EXAMPLE 2

Preparation of Intermediate 1 (Second Synthetic Route)

Sodium tungsten (0.14 g, 0.44 mmol) dissolved in H$_2$O (0.5 ml) and, dropwise, a solution of H$_2$O$_2$ (35%, 4.7 g, 49 mmol) in H$_2$O (4 ml) were added successively to a solution of azithromycin (35 g, 44.6 mmol) in methanol (350 ml). The reaction mixture was stirred at room temperature for 16 h, diluted with water (350 ml), and the methanol was evaporated under vacuum. The aqueous solution was diluted with citric acid (5% aqueous solution) (0.5 L), washed with CH$_2$Cl$_2$ (2×250 ml) and, after adding conc. NH$_3$ until pH=9 was obtained, it was extracted with CH$_2$Cl$_2$ (3×0.4 L). The organic phase was dehydrated with sodium sulfate, filtered and evaporated under vacuum to give intermediate 1 (28.1 g, yield 82%) as a white solid.

[M+I]$^+$ 766

EXAMPLE 3

Preparation of Compound 1

Conc. HCl (8 ml) was added dropwise to a solution of intermediate 1 (28 g, 36.6 mmol) in methanol (800 ml) and the reaction mixture was stirred for 3 h. After it had been neutralized with conc. NH$_3$ the solution was evaporated from the solvent. The raw product was dissolved in 1 N HCl and washed with CH$_2$Cl$_2$ (3×100 ml) and K$_2$CO$_3$ was added to the aqueous phase until an alkaline pH was obtained. Extraction with ethyl acetate (4×100 ml) gave an organic phase which, after being dehydrated with sodium sulfate and filtered, gave compound 1 (225 mg, yield 90%) as a white solid.

[M+I]$^+$ 607

EXAMPLE 4

Preparation of Intermediate 2

Intermediate 2 was obtained as by-product during synthesis of intermediate 1. Its yield can be maximized by using an excess of oxidant.

[M+I]$^+$ 782

HPLC-MS: Zorbax SB-C18 column, 2.1×50 mm, 3.5 mm; column temperature 45° C.; mobile phase A 0.1% formic acid in H$_2$O, B 0.1% formic acid in acetonitrile; gradient 0 min 5% of B, 8 min 95% of B; flow rate 1 ml/min; injection volume 2 μl; sample concentration 0.5-1 mg/ml; detector: mass spectrometer equipped with electrospray ionization source, positive ionization; retention time 2.75 min; total run time 8 min plus 2 min of re-equilibration.

EXAMPLE 5

Preparation of Compound 2

Compound 2 was prepared from intermediate 2 (220 mg, 0.28 mmol) following the procedure described for the synthesis of compound 1. Purification by means of chromatography Variant Mega Bond Elut (silica 10 g cartridge, eluent from $CH_2Cl_2$ to $CH_2Cl_2MeOH/NH_3$ 85/15/1.5) gave compound 2 (106 mg, yield 60%).

$[M+I]^+$ 623

EXAMPLE 6

Preparation of Intermediate 3

A heterogeneous solution of intermediate 1 (2.5 g, 3.26 mmol) in DMF (35 ml) was stirred for suspension for 40 minutes in the presence of a stream of nitrogen. The solution was cooled to room temperature, evaporated from the DMF and, after dilution with water and ethyl acetate, the organic phase was extracted, and the aqueous phase was washed with ethyl acetate. The combined organic solution was washed with a 20% NaCl solution, dehydrated with sodium sulfate, filtered and evaporated from the solvent at room temperature. Purification by means of Biotage chromatography (silica 40M cartridge, eluent $CH_2Cl_2/MeOH/NH_3$ 90/3/0.3) gave intermediate 3 (1.1 g, yield 45%).

$[M+I]^+$ 705

EXAMPLE 7

Preparation of Compound 3

Compound 3 was prepared from intermediate 3 (237 mg, 0.336 mmol) following the procedure described for the synthesis of compound 1. Purification by chromatography Variant Mega Bond Elut (silica 20 g cartridge, eluent from $CH_2Cl_2$ to $CH_2Cl_2/MeOH/NH_3$ 95/5/0.5) gave compound 3 (110 mg, yield 60%).

$[M+I]^+$ 546

EXAMPLE 8

Preparation of Intermediate 4

Intermediate 4 was prepared from 3'-dedimethylamino-erythromycin A oxime (3 g, 4.25 mmol) obtained by oxidation, pyrolysis and reduction of erythromycin A oxime as described in international patent application WO 00/42055 example 6 in the name of Zambon Group, following the procedures described in the literature (Djokic S. et al., J. Chem. Soc. Perkin Trans., 1986, 1881). Intermediate 4 (2.8 g, yield 95%) was obtained as a white solid.

$[M+I]^+$ 692

HPLC-MS: Zorbax SB-C18 column, 2.1×50 mm, 3.5 mm; column temperature 45° C.; mobile phase A 0.1% formic acid in $H_2O$, B 0.1% formic acid in acetonitrile; gradient 0 min 5% of B, 8 min 95% of B; flow rate 1 ml/min; injection volume 2 μl; sample concentration 0.5-1 mg/ml; detector: mass spectrometer equipped with electrospray ionization source, positive ionization; retention time 4.99 min; total run time 8 min plus 2 min of re-equilibration.

EXAMPLE 9

Preparation of Intermediate 5

A solution of intermediate 4 (2 g, 2.89 mmol), formic acid (0.22 ml, 5.78 mmol) and formaldehyde in chloroform (25 ml) was placed under reflux for 4 h. The cold solution was diluted with a solution of NaCl at 20% and conc. $NH_3$, the organic phase was extracted and the aqueous phase was washed with ethyl acetate. The combined organic solution was dehydrated with sodium sulfate, filtered and evaporated under vacuum to give a solid (2.2 g). Purification by Biotage chromatography (silica 40M cartridge, eluent $CH_2Cl_2/MeOH/NH_3$ 98/2/0.2) gave intermediate 5 (1.57 g, yield 77%) as a crystalline solid.

$[M+I]^+$ 707

EXAMPLE 10

Preparation of Compound 4

Compound 4 was prepared from intermediate 5 (200 mg, 0.28 mmol) following the procedure described for the synthesis of compound 1. Purification by Biotage chromatography (silica 12M cartridge, eluent $CH_2Cl_2/MeOH/NH_3$ 98/2/0.2) gave compound 4 (150 mg, yield 97%).

$[M+I]^+$ 549

EXAMPLE 11

Preparation of Intermediate 7

A solution of acetyl chloride (0.052 ml, 0.68 mmol) in $CH_2Cl_2$ (1 ml) was added dropwise at 0° C. to a solution of intermediate 6 (0.5 g, 0.68 mmol), obtained from azithromycin following the procedure described in U.S. Pat. No. 5,250,518 in the name of Pliva, and triethylamine (0.14 ml, 1 mmol) in $CH_2Cl_2$ (15 ml) and THF (15 ml), and was stirred at room temperature for 16 h. The reaction mixture was evaporated from the solvent, diluted with $CH_2Cl_2$ and washed with a 20% solution of NaCl to give a solid raw product. Purification by Biotage chromatography (silica 40S cartridge, eluent $CH_2Cl_2/MeOH/NH_3$ 97/3/0.3) gave intermediate 7 (460 mg, yield 87%).

$[M+I]^+$ 778

EXAMPLE 12

Preparation of Compound 5

Compound 5 was prepared from intermediate 7 (370 mg, 0.48 mmol) following the procedure described for the synthesis of compound 1. Purification by Biotage chromatography (silica 12M cartridge, eluent $CH_2Cl_2/MeOH/NH_3$ 98/2/0.2) gave compound 5 (260 mg, yield 85%).

$[M+I]^+$ 620

EXAMPLE 13

Preparation of 2-(thiazol-2-yl-amino)-ethanol (Intermediate 8)

3A molecular sieves (1 g) and a solution of 2-thiazole carboxyaldehyde (1 g, 8.84 mmol) in ethanol (30 ml) were added to a solution of 2-aminoethanol (570 mg, 9.33 mmol) in ethanol (40 ml) in a nitrogen atmosphere. The reaction mixture was stirred for 3 h, filtered through a celite diaphragm to remove the molecular sieves, acetic acid (1 ml) and Pd/C 10% (0.7 g) were added, and then it was held under a p.s.i. of 30 for 2 h. Filtration through a celite diaphragm and evaporation under vacuum gave a solid raw product that was purified by flash chromatography (silica, eluent $CH_2Cl_2$/MeOH/$NH_3$ 90/8/0.8) to give intermediate 8 (1 g, yield 70%).

[M+I]$^+$ 159

$CDCl_3$: 7.69 and 7.25 (2m, 2H, Th); 4.14 (s, 2H, $CH_2$Th); 3.66 (m, 2H, $CH_2$O; 2.85 (m, 2H, $CH_2$N); 2.3 (broad s, 2H, NH+OH).

EXAMPLE 14

Preparation of 9H-fluoren-9-yl-methyl ester of (2-hydroxy-ethyl)-thiazol-2-yl-carbamic acid (Intermediate 9)

A solution of $NaHCO_3$ (960 mg, 11.4 mmol) in $H_2O$ (20 ml) and a solution of 9H-fluoren-9-yl-methyloxycarbonyl chloroformate (1.57 g, 6 mmol) in dioxan (10 ml) were added dropwise and simultaneously to a solution of intermediate 8 (900 mg, 5.7 mmol) in dioxan (20 ml). The reaction mixture was stirred for 2 h, diluted with water and extracted with ethyl acetate. The combined organic phase was washed with citric acid (5% aqueous solution), dehydrated with sodium sulfate, filtered and evaporated under vacuum. Purification by flash chromatography (silica, eluent ethyl acetate/petroleum ether 4/1) gave intermediate 9 (1.92 g, yield 88%).

[M+I]$^+$ 381

$CDCl_3$: 7.2-7.8 (m, 10H, Th+Fmoc); 4.95 and 5.17 (2m, 1H, CH); 4.68 (m, 2H, $CH_2$Th); 4.58 (m, 2H, $CH_2$-Fmoc); 3.4-3.8 (m, 5H, $CH_2CH_2OH$).

EXAMPLE 15

Preparation of 9H-fluoren-9-yl-methyl ester of (2-oxo-ethyl)-thiazol-2-yl-carbamic acid (Intermediate 10)

TEMPO (3 mg, 0.019 mmol), a solution of KBr (19 mg, 0.157 mmol) in $H_2O$ (1 ml) and, dropwise, a solution of sodium hypochlorite (1.6 ml, 2.86 mmol) and $NaHCO_3$ (120 mg, 1.4 mmol) in $H_2O$ (5 ml) were added sequentially, at 0° C., to a solution of intermediate 9 (0.6 g, 1.57 mmol) in $CH_2Cl_2$. The reaction mixture was added for 2 h, diluted with ethyl acetate and sat. NaCl, the aqueous phase was separated and washed with ethyl acetate (3×20 ml). The combined organic phase was washed with sat. NaCl, dehydrated with sodium sulfate, filtered and evaporated under vacuum to give intermediate 10 (560 mg, yield 93%) as an oil.

[M+I]$^+$ 379

$CDCl_3$: 9.2 and 9.6 (2s, 1H, CHO); 7.2-7.8 (m, 10H, Th+Fmoc); 4.0-4.9 (m, 7H, 3$CH_2$+CH).

EXAMPLE 16

Preparation of Intermediate 12

A mixture of intermediate 11 (16 g, 21.7 mmol), obtained from erythromycin A oxime as described in the literature (Djokic S. et al., J. Chem. Soc. Perkin Trans., 1986, 1881), in acrylonitrile (160 ml) was refluxed for 7 h and evaporated under vacuum from the acrylonitrile in excess to give a solid raw product. Purification by flash chromatography (silica, eluent $CH_2Cl_2$/MeOH/$NH_3$ 90/5/0.5) gave intermediate 12 (6.9 g, yield 41%).

EXAMPLE 17

Preparation of Intermediate 13

Rh (5% on $Al_2O_3$, 1 g) was added to a mixture of intermediate 12 (5 g, 6.3 mmol) and a solution of $NH_3$ in ethanol (1.5 M, 60 ml). After three cycles of hydrogenation, the reaction mixture was stirred for 6 h in a hydrogen atmosphere of 35 p.s.i. Filtration through a celite diaphragm, evaporation under vacuum and purification by flash chromatography (silica, eluent-$CH_2Cl_2$/MeOH/$NH_3$ 85/15/1.5) gave intermediate 13 (3.6 g, yield 57%).

EXAMPLE 18

Preparation of Intermediate 14

Intermediate 14 was prepared from intermediate 13 (2.15 g, 2.71 mmol) following the procedure described for the synthesis of compound 1.

Purification by Biotage chromatography (silica 40S cartridge, eluent $CH_2Cl_2$/MeOH/$NH_3$ 85/15/1.5) gave intermediate 14 (1.6 g, yield 92%).

[M+I]$^{2+}$/2 318

HPLC-MS: Zorbax SB-C18 column, 2.1×50 mm, 3.5 mm; column temperature 45° C.; mobile phase A 0.1% formic acid in $H_2O$, B 0.1% formic acid in acetonitrile; gradient 0 min 5% of B, 8 min 95% of B; flow rate 1 ml/min; injection volume 2 μl; sample concentration 0.5-1 mg/ml; detector: mass spectrometer equipped with electrospray ionization source, positive ionization; retention time 0.21 min; total run time 8 min plus 2 min of re-equilibration.

EXAMPLE 19

Preparation of Compound 6

3A molecular sieves (1 g) and thiazole-2-carboxyaldehyde (65 mg, 0.552 mmol) were added sequentially to a solution of intermediate 14 (350 mg, 0.552 mmol) in ethanol (1 ml). The solution was stirred for 3 h, filtered through a celite diaphragm to remove the molecular sieves, and Pd/C 10% (35 mg) was added. After three cycles of hydrogenation, the reaction mixture was stirred for 2 h in a hydrogen atmosphere of 20 p.s.i. Filtration through a celite diaphragm and evaporation under vacuum gave a solid raw product which was purified by Biotage chromatography (silica 12M cartridge, eluent $CH_2Cl_2$/MeOH/$NH_3$ 90/6/0.6) to give compound 6 (54 mg, yield 13%).

[M+I]$^+$ 732

EXAMPLE 20

Preparation of Compound 7

3A molecular sieves (1 g) and thiazole-2-furaldehyde (61 mg, 0.63 mmol) were added sequentially to a solution of intermediate 14 (0.4 g, 0.63 mmol) in ethanol (8 ml). The reaction mixture was stirred for 6 h, filtered through a celite diaphragm, $NaBH_4$ (29 mg, 0.75 mmol) was added, and stirring was continued for a further 16 h. After neutralization by addition of acetic acid and stirring for 2 h, the solution was neutralized with conc. $NH_3$ and evaporated. The raw mixture was diluted with $CH_2Cl_2$, filtered from the inorganic salts and purified by Biotage chromatography (silica 12M cartridge, eluent $CH_2Cl_2$/MeOH/$NH_3$ 95/5/0.5) to give compound 7 (24 mg, yield 6%).

[M+I]$^{2+}$/2 358

EXAMPLE 21

Preparation of compound 8

Compound 8 was prepared from intermediate 14 (0.35 g, 0.552 mmol) following the procedure described for compound 7, but with imidazole-4-carboxyaldehyde (54 mg, 0.552 mmol) instead of the 2-furaldehyde. The raw product was purified by Biotage chromatography (silica 12M cartridge, eluent $CH_2Cl_2/MeOH/NH_3$ 90/7/0.7) to give compound 8 (24 mg, yield 7%).

$[M+I]^{2+}/2$ 358

EXAMPLE 22

Preparation of Compound 9

Compound 9 was prepared from intermediate 14 (0.35 g, 0.552 mmol) following the procedure described for compound 7, but using 2-thiophene-carboxyaldehyde (64 mg, 0.552 mmol) instead of the 2-furaldehyde. The raw product was purified by Varian Mega Bond Eliot chromatography (silica 20 g cartridge, eluent from $CH_2Cl_2$ to $CH_2Cl_2/MeOH/NH_3$ 90/10/1) to give compound 9 (22 mg, yield 6%).

$[M+I]^{2+}/2$ 366

EXAMPLE 23

Preparation of Intermediate 15

A solution of intermediate 14 (0.845 g, 1.33 mmol) in dichloroethane (20 ml) was held in an argon atmosphere, and the following were added sequentially: 3A molecular sieves (3 g), acetic acid (0.152 ml, 2.66 mmol), a solution of intermediate 10 (0.56 g, 1.4 mmol) in dichloroethane (10 ml) and tetramethyl-ammonium-triacetoxyboron hydride (0.596 g, 2.26 mmol). The reaction mixture was stirred for 16 h, filtered through a celite diaphragm and evaporated under vacuum. Purification by Biotage chromatography (silica 40M cartridge, eluent $CH_2Cl_2/MeOH/NH_3$ 90/6/0.6) gave intermediate 15 (390 mg, yield 30%).

$[M+I]^{2+}/2$ 499

HPLC-MS: Zorbax SB-C18 column, 2.1×50 mm, 3.5 mm; column temperature 45° C.; mobile phase A 0.1% formic acid in $H_2O$, B 0.1% formic acid in acetonitrile; gradient 0 min 5% of B, 8 min 95% of B; flow rate 1 ml/min; injection volume 2 μl; sample concentration 0.5-1 mg/ml; detector: mass spectrometer equipped with electrospray ionization source, positive ionization; retention time 3.15 min; total run time 8 min plus 2 min re-equilibration.

EXAMPLE 24

Preparation of Compound 10

Piperidine (1 ml) was added dropwise to a solution of intermediate 15 (390 mg, 0.39 mmol) in DMF (5 ml) and the reaction mixture was stirred for 1. After dilution with sat. NaCl, the compound was extracted with ethyl acetate and the corresponding organic phase was dehydrated with sodium sulfate, filtered and evaporated. Purification by Varian Mega Bond Eliot chromatography (silica 20 g cartridge, eluent from $CH_2Cl_2$ to $CH_2Cl_2/MeOH/NH_3$ 90/10/1) gave compound 10 (249 mg, yield 82%).

$[M+I]^{2+}/2$ 388

EXAMPLE 25

Preparation of Intermediate 16

Intermediate 16 was prepared from intermediate 13 (0.6 g, 0.75 mmol) and benzaldehyde (77 ml, 0.75 mmol) following the procedure described for compound 6. Purification by flash chromatography (silica, eluent $CH_2Cl_2/MeOH/NH_3$ 90/10/1) gave intermediate 16 (0.27 g, yield 41%).

$[M+I]^+$ 882

EXAMPLE 26

Preparation of Compound 11

Compound 11 was prepared from intermediate 16 (65 mg, 0.072 mmol) following the procedure described for the synthesis of compound 1. Purification by flash chromatography (silica, eluent $CH_2Cl_2/MeOH/NH_3$ 90/10/1) gave compound 11 (47 mg, yield 90%).

$[M+I]^+$ 725

EXAMPLE 27

Preparation of Intermediate 17

Intermediate 17 was prepared from intermediate 13 (3.28 g, 4.15 mmol) and from benzyl (6-oxo-hexyl)-carbamate (1.03 g, 4.15 mmol) following the procedure described for the synthesis of compound 6. Purification by flash chromatography (silica, eluent $CH_2Cl_2/MeOH/NH_3$ 90/10/1) gave intermediate 17 (320 mg, yield 60%).

$[M+I]^+$ 1026

EXAMPLE 28

Preparation of Intermediate 18

Intermediate 18 was prepared from intermediate 17 (2.2 g, 2.15 mmol) following the procedure described for the synthesis of intermediate 13 using Pd/C 10% (0.2 g) instead of Rh as catalyst. Purification by flash chromatography (silica, eluent $CH_2Cl_2/MeOH/NH_3$ 88/12/1.2) gave intermediate 18 (1.8 g, yield 91%).

$[M+I]^+$ 892

EXAMPLE 29

Preparation of Intermediate 19

Intermediate 19 was prepared from intermediate 18 (400 g, 0.1 mmol) following the procedure described for the synthesis of compound 6. Purification by flash chromatography (silica, eluent $CH_2Cl_2/MeOH/NH_3$ 88/12/1.2) gave intermediate 19 (320 mg, yield 73%).

$[M+I]^+$ 982

EXAMPLE 30

Preparation of Compound 12

Compound 12 was prepared from intermediate 19 (97 mg, 0.099 mmol) following the procedure described for the synthesis of compound 1. Purification by flash chromatography (silica, eluent $CH_2Cl_2/MeOH/NH_3$ 90/10/1) gave compound 12 (43 mg, yield 80%).

$[M+I]^+$ 824

EXAMPLE 31

Preparation of Intermediate 20

Intermediate 20 was prepared from intermediate 4 (2.7 g, 3.9 mmol) following the procedure described for the synthesis of intermediate 12. Purification by flash chromatography (silica, eluent $CH_2Cl_2/MeOH/NH_3$ 95/5/0.5) gave intermediate 20 (2.5 g, yield 86%).

$[M+I]^+$ 746

EXAMPLE 32

Preparation of Intermediate 21

$NH_3$ in methanol (30 ml, 1.7 M solution) and Rh (5% on $Al_2O_3$, 0.48 g) were added to a solution of intermediate 20 (2.4 g, 3.2 mmol) in methanol (30 ml), and the reaction mixture was stirred for 3 h under a hydrogen atmosphere of 35 p.s.i. Filtration through a celite diaphragm, evaporation under vacuum and purification by flash chromatography (silica, eluent $CH_2Cl_2$/MeOH/$NH_3$ 90/10/1) gave intermediate 21 (1.8 g, yield 75%).

$[M+I]^+$ 750

EXAMPLE 33

Preparation of Intermediate 22

Intermediate 22 was prepared from intermediate 21 (633 mg, 0.85 mmol) and from intermediate 10 (320 mg, 0.85 mmol) following the procedure described for the synthesis of intermediate 15. Purification by flash chromatography (silica, eluent $CH_2Cl_2$/MeOH/$NH_3$ 95/5/0.5) gave intermediate 22 (200 mg, yield 22%).

$[M+I]^+$ 1112

HPLC-MS: Zorbax SB-C18 column, 2.1×50 mm, 3.5 mm; column temperature 45° C.; mobile phase A 0.1% formic acid in $H_2O$, B 0.1% formic acid in acetonitrile; gradient 0 min 5% of B, 8 min 95% of B; flow rate 1 ml/min; injection volume 2 µl; sample concentration 0.5-1 mg/ml; detector: mass spectrometer equipped with electrospray ionization source, positive ionization; retention time 4.18 min; total run time 8 min plus 2 min of re-equilibration.

EXAMPLE 34

Preparation of Intermediate 23

Intermediate 23 was prepared from intermediate 22 (190 mg, 0.17 mmol) following the procedure described for the synthesis of compound 10. Purification by gravity chromatography (silica, eluent $CH_2Cl_2$/MeOH/$NH_3$ 90/10/1) gave intermediate 23 (200 mg, yield 60%).

$[M+I]^+$ 890

EXAMPLE 35

Preparation of Compound 13

Compound 13 was prepared from intermediate 23 (90 mg, 0.1 mmol) following the procedure described for the synthesis of compound 1. Purification by Biotage chromatography (silica 12M cartridge, eluent $CH_2Cl_2$/MeOH/$NH_3$ 95/5/0.5) gave compound 13 (45 mg, yield 61%).

$[M+I]^+$ 732

EXAMPLE 36

Preparation of Intermediate 24

Intermediate 24 was prepared from intermediate 21 (0.5 g, 0.67 mmol) and 2-thiazolecarboxyaldehyde (76 mg, 0.67 mmol) following the procedure described for the synthesis of compound 6. The raw product was purified by gravity chromatography (silica, eluent from $CH_2Cl_2$/MeOH/$NH_3$ 90/10/0 to $CH_2Cl_2$/MeOH/$NH_3$ 90/10/1) to give intermediate 24 (250 mg, yield 44%).

$[M+I]^+$ 848

EXAMPLE 37

Preparation of Compound 14

Compound 14 was prepared from intermediate 24 (150 mg, 0.177 mmol) following the procedure described for the synthesis of compound 1. Purification by flash chromatography (silica, eluent $CH_2Cl_2$/MeOH/$NH_3$ 90/9/0.9) gave compound 14 (100 mg, yield 48%).

$[M+I]^+$ 689

EXAMPLE 38

Pharmacological Activity In Vivo:

A) Acute Contact Dermatitis.

Animals

Groups of 5-6 CD1 mice (18-24 g) were used.

Administration of the Compounds

All the macrolide derivatives were dissolved in Trans-phase Delivery System (TPDS), a vehicle containing benzyl alcohol 10%, acetone 40% and isopropanol 50%.

15 microliters of the compounds (500 µg), dissolved in TPDS, were applied topically to the internal surface of one ear; 30 minutes later, 12 microliters of a solution of tetradecanoyl phorbol acetate (TPA) at a concentration of 0.01% dissolved in acetone, were applied to the same area.

Six hours later, the animals were sacrificed by inhalation of $CO_2$.

Evaluation of the Results

Two methods were used for assessing the auricular edema:
a) Weighing a defined portion of auricular pinna.
b) Measurement of auricular thickness using precision spring calipers.

The degree of edema was calculated by subtracting the weight or the thickness of the untreated ear from that of the treated contralateral ear. To determine the degree of remission of the edema, the difference (weight or thickness) of the groups treated with TPA+macrolides relative to those treated with just TPA was compared.

The activity of the macrolides was measured using the modified method of Zunic et al. (1998): MDL (Lysyl) GDP, a non-toxil muramyl dipeptide derivative inhibits cytokine production by activated macrophages and protects mice from phorbol ester- and oxazolone-induced inflammation (J. Invest. Dermatol., 111 (1), 77-82).

The data relating to erythromycin and azithromycin refer to treatment in a single dose at 500 µg/ear.

The results obtained for some compounds of formula I, representative of the entire class, are shown in the following table.

| Compound | Edema (inhibition %) | Method of measurement of the edema |
|---|---|---|
| Erythromycin | 42 | a |
| Azithromycin | 40 | a |
| 1 | 56.7 | a |
| 2 | 25.3 | a |
| 3 | 34.4 | a |
| 4 | 16.5 | a |
| 5 | 40.5 | a |
| 8 | 29.7 | a |
| 12 | 39.5 | b |
| 13 | 44.7 | a |

EXAMPLE 39

B) LPS-Induced Pulmonary Inflammation in the Rat

Administration

The rats were given a single dose of 0.4 mg/kg of LPS (*E. coli*, serotype 026:6) endotracheally, by the trans-oral route. Tracheal instillation was carried out under halothane anesthesia and 20 hours after the endotracheal administration of LPS/saline solution the animals were sacrificed by urethane overdose.

Washing

The lungs were washed with four aliquots each of 5 ml of saline solution with heparin 10 IU/ml. The cellular suspension was concentrated by low-speed centrifugation and the cellular pellet was suspended.

Cell Count and Differentiation

The total cell count was obtained using a hemocytometer.

The differential count was obtained from cytospin preparations stained with May-Grunwald-Giemsa (Tamaoki J., Tagaya E., Yamawaki I., Sakai N., Nagai A., Konno K., 1995. Effect of erythromycin on endotoxin-induced microvascular leakage in the rat trachea and lungs. Am. J. Respir. Crit. Care Med., 151, 1582-8). The rats received the test compounds orally at a dose of 100, 40 and 10 μmol/kg as a single dose administered orally one hour before exposure to LPS.

The ED/50 value is the dose that caused 50% reduction in the neutrophil count in the bronchial wash fluid.

The result for erythromycin relates to oral treatment in a single dose with 130 μmol/kg.

The result obtained for compound I is shown in the following table.

| Compound | ED/50 μmol/kg |
|---|---|
| erythromycin | not active |
| 1 | 10 |

Similar results were obtained with the other compounds of formula I mentioned in the examples.

EXAMPLE 40

Pharmacological Activity In Vitro:

Antibiotic Activity

Preparation for the Test

All the compounds were dissolved in DMSO as concentrated solution 100× at a concentration of 12.8 mg/ml. The concentrated solution was diluted 1:100 in the incubation medium to a final concentration of 128 μg/ml (DMSO 1% final concentration). To evaluate the MIC, successive dilutions 1:2 of the 100× concentrated solution will be prepared in DMSO and diluted 1:100 in the incubation medium.

Experimental Method

The MIC (minimum inhibitory concentration) values or antibiotic activity at 128 μg/ml were evaluated for the compounds.

The MIC values were determined in liquid culture medium by the technique described in the "Manual of Clinical Microbiology, 7th edition (1999), American Society for Microbiology".

The following bacterial strains were used:
*Streptococcus pneumoniae* ATCC 49619
*Staphylococcus aureus* ATCC 29213 or ATCC 6538
*Enterococcus faecalis* ATCC 29212
*Streptococcus pyogenes* ATCC 19615

Evaluation of the Results

The results are expressed as MIC (μg/ml), evaluated as the lowest concentration of the test substance that completely inhibits growth visible to the naked eye.

All the compounds in the examples were tested and the results obtained for some of them, representative of the entire class of compounds of formula I, are shown in the following table.

| Compounds | Sta. aureus ATCC 29213 MIC (μg/ml) | Str. pneum. ATTC 49619 MIC (μg/ml) | Enter. faec. ATCC 29212 MIC (μg/ml) | Sta. aureus ATCC 6538 128 (μg/ml) | Str. pyogen. ATTC 19615 128 (μg/ml) |
|---|---|---|---|---|---|
| Erythromycin | 0.25 | 0.12 | 1 | — | — |
| 12 | >128 | 64 | >128 | — | — |
| 6 | 64 | 8 | 64 | — | — |
| 1 | — | — | >128 | not active | not active |

The results given in the table clearly show that the compounds of formula I, of the present invention, are substantially devoid of antibiotic activity.

The invention claimed is:

1. A compound of formula

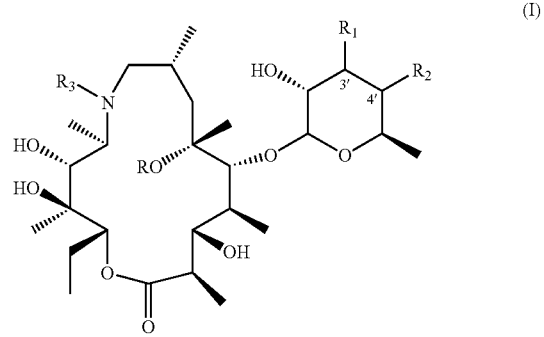

(I)

in which

R is a hydrogen atom or a methyl $R_1$ is a hydrogen atom, an N,N-di-($C_1$-$C_3$)-alkylamino group, an N,N-di-($C_1$-$C_3$)-alkylamino-N-oxide group, an N—($C_1$-$C_4$)-acyl-N—($C_1$-$C_3$)-alkylamino group or together with $R_2$ forms a bond between the carbon atoms at 3' and 4';

$R_2$ is a hydrogen atom or together with $R_1$ forms a bond between the carbon atoms at 3' and 4';

$R_3$ is a linear or branched $C_1$-$C_5$ alkyl, a benzyl optionally substituted with one or two substituents selected from nitro, hydroxy, carboxy, amino, linear or branched $C_1$-$C_5$ alkyl, $C_1$-$C_4$ alkoxy groups, $C_1$-$C_4$ alkoxycarbonyl groups, aminocarbonyl groups or cyano or a chain of formula —$(CH_2)$r-X—$(CH_2)$m-Y—$(CH_2)$n-A in which A is a hydrogen atom, a phenyl or a heteroaryl with five or six members containing from one to three atoms selected from nitrogen, oxygen and sulfur;

X represents O, S, SO, $SO_2$, $NR_6$ and $R_6$ is a hydrogen atom, a linear or branched $C_1$-$C_3$ alkyl, a $C_1$-$C_3$ alkoxycarbonyl group, a benzyloxycarbonyl group;

Y is a $C_6H_4$ group, a heteroaryl with five or six members containing from one to three atoms selected from nitrogen, oxygen and sulfur or represents O, S, SO, $SO_2$, $NR_6$ where $R_6$ has the meanings given above;

r is an integer of from 1 to 3;

m is an integer of from 1 to 6;

n is an integer of from 0 to 2;

moreover the nitrogen atom to which $R_3$ is bound can be present in the N-oxide form;

and their pharmaceutically acceptable salts;

provided that when R is a hydrogen atom and $R_1$ is a dimethylamino group, $R_3$ is different from a ($C_1$-$C_5$)-alkyl group.

2. A compound according to claim 1 in which $R_1$ is a hydrogen atom, an N-methyl-N—$(C_1$-$C_3)$-alkylamino group, an N-methyl-N—$(C_1$-$C_3)$-alkylamino-N-oxide group, an N—$(C_1$-$C_4)$-acyl-N-methylamino group or $R_1$ together with $R_2$ forms a bond between the carbon atoms at 3' and 4'.

3. A compound according to claim 2 in which $R_1$ is a hydrogen atom, an N,N-dimethylamino group, an N,N-dimethylamino-N-oxide group, an N-acetyl-N-methylamino group or $R_1$ together with $R_2$ forms a bond between the carbon atoms at 3' and 4'.

4. A compound according to claim 1 in which $R_3$ is a linear or branched $(C_1$-$C_3)$ alkyl, a benzyl optionally substituted with one or two substituents selected from nitro, hydroxy, carboxy, amino, linear or branched $(C_1$-$C_3)$ alkyl, $C_1$-$C_4$ alkoxy and cyano groups or a chain of formula

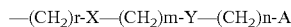
—(CH$_2$)r-X—(CH$_2$)m-Y—(CH$_2$)n-A in which
A is a hydrogen atom, a phenyl or a heteroaryl with five or six members containing from one to three atoms selected from nitrogen, oxygen and sulfur;
X is O or $NR_6$ and $R_6$ is a hydrogen atom, a linear or branched $C_1$-$C_3$ alkyl;
Y, when n is 0, is a $C_6H_4$ group or a heteroaryl with five or six members containing from one to three atoms selected from nitrogen, oxygen and sulfur; or, when n is different from 0, it is O or $NR_6$ and $R_6$ is a hydrogen atom, a linear or branched $C_1$-$C_3$ alkyl;
r is an integer of from 1 to 3;
m is an integer selected from 1 and 2;
n is an integer of from 0 to 2;
moreover the nitrogen atom to which $R_3$ is bound can be present in the N-oxide form.

5. A compound according to claim 4 in which $R_3$ is a methyl, a benzyl or a chain of formula

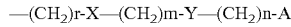
—(CH$_2$)r-X—(CH$_2$)m-Y—(CH$_2$)n-A in which
A is a hydrogen atom, a phenyl or a heteroaryl with five or six members selected from pyrrole, thiophene, furan, imidazole, oxazole, thiazole, pyridine, pyrimidine, triazole and thiadiazole;
X is O or $NR_6$ and $R_6$ is a hydrogen atom;
Y, when n is 0, is a $C_6H_4$ group or a heteroaryl with five or six members selected from pyrrole, thiophene, furan, imidazole, oxazole, thiazole, pyridine, pyrimidine, triazole and thiadiazole; or, when n is 1, it is $NR_6$ and $R_6$ is a hydrogen atom;
r is an integer of from 1 to 3;
m is an integer selected from 1 and 2;
n is an integer selected from 0 and 1;
moreover the nitrogen atom to which $R_3$ is bound can be present in the N-oxide form.

6. A compound according to claim 5 in which $R_3$ is a methyl, a benzyl or a chain of formula

—(CH$_2$)r-X—(CH$_2$)m-Y—(CH$_2$)n-A in which
A is a hydrogen atom, a phenyl or a heteroaryl selected from thiophene, furan, imidazole, thiazole, pyridine and triazole;
X is $NR_6$ and $R_6$ is a hydrogen atom;
Y, when n is 0, is a $C_6H_4$ group or a heteroaryl selected from thiophene, furan, imidazole, thiazole, pyridine and triazole; or, when n is 1, it is $NR_6$ and $R_6$ is a hydrogen atom;
r is 3;
m is an integer selected from 1 and 2;
n is an integer selected from 0 and 1;
moreover the nitrogen atom to which $R_3$ is bound can be present in the N-oxide form.

7. A compound according to claim 1, in which $R_1$ is a hydrogen atom, an N-methyl-N—$(C_1$-$C_3)$-alkylamino group, an N-methyl-N—$(C_1$-$C_3)$-alkylamino-N-oxide group, an N—$(C_1$-$C_4)$-acyl-N-methylamino group or $R_1$ together with $R_2$ forms a bond between the carbon atoms at 3' and 4';
at the same time $R_3$ is a linear or branched $(C_1$-$C_3)$ alkyl, a benzyl optionally substituted with one or two substituents selected from nitro, hydroxy, carboxy, amino, linear or branched $(C_1$-$C_3)$ alkyl, $C_1$-$C_4$ alkoxy and cyano groups or a chain of formula

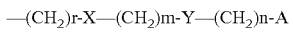
—(CH$_2$)r-X—(CH$_2$)m-Y—(CH$_2$)n-A in which
A is a hydrogen atom, a phenyl or a heteroaryl with five or six members containing from one to three atoms selected from nitrogen, oxygen and sulfur;
X is O or $NR_6$ and $R_6$ is a hydrogen atom, a linear or branched $C_1$-$C_3$ alkyl;
Y, when n is 0, is a $C_6H_4$ group or a heteroaryl with five or six members containing from one to three atoms selected from nitrogen, oxygen and sulfur; or, when n is different from 0, it is O or $NR_6$ and $R_6$ is a hydrogen atom, a linear or branched $C_1$-$C_3$ alkyl;
r is an integer of from 1 to 3;
m is an integer selected from 1 and 2;
n is an integer of from 0 to 2;
moreover the nitrogen atom to which $R_3$ is bound can be present in the N-oxide form.

8. A compound according to claim 7 in which $R_3$ is a methyl, a benzyl or a chain of formula

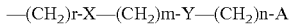
—(CH$_2$)r-X—(CH$_2$)m-Y—(CH$_2$)n-A in which
A is a hydrogen atom, a phenyl or a heteroaryl with five or six members selected from pyrrole, thiophene, furan, imidazole, oxazole, thiazole, pyridine, pyrimidine, triazole and thiadiazole;
X is O or $NR_6$ and $R_6$ is a hydrogen atom;
Y, when n is 0, is a $C_6H_4$ group or a heteroaryl with five or six members selected from pyrrole, thiophene, furan, imidazole, oxazole, thiazole, pyridine, pyrimidine, triazole and thiadiazole; or, when n is 1, it is $NR_6$ and $R_6$ is a hydrogen atom;
r is an integer of from 1 to 3;
m is an integer selected from 1 and 2;
n is an integer selected from 0 and 1;
moreover the nitrogen atom to which $R_3$ is bound can be present in the N-oxide form.

9. A compound according to claim 8 in which $R_3$ is a methyl, a benzyl or a chain of formula

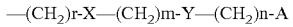
—(CH$_2$)r-X—(CH$_2$)m-Y—(CH$_2$)n-A in which
A is a hydrogen atom, a phenyl or a heteroaryl selected from thiophene, furan, imidazole, thiazole, pyridine and triazole;
X is $NR_6$ and $R_6$ is a hydrogen atom;
Y, when n is 0, is a $C_6H_4$ group or a heteroaryl selected from thiophene, furan, imidazole, thiazole, pyridine and triazole; or, when n is 1, it is $NR_6$ and $R_6$ is a hydrogen atom;
r is 3;
m is an integer selected from 1 and 2;
n is an integer selected from 0 and 1;
moreover the nitrogen atom to which $R_3$ is bound can be present in the N-oxide form.

10. A compound according to claim 9 in which $R_1$ is a hydrogen atom, an N,N-dimethylamino group, an N,N-dimethylamino-N-oxide group, an N-acetyl-N-methylamino group or $R_1$ together with $R_2$ forms a bond between the carbon atoms at 3' and 4'.

11. A process for preparing a compound according to claim 1 that comprises the removal of the L-cladinose at position 3, through a reaction of hydrolysis, from the azithromycin derivatives of formula

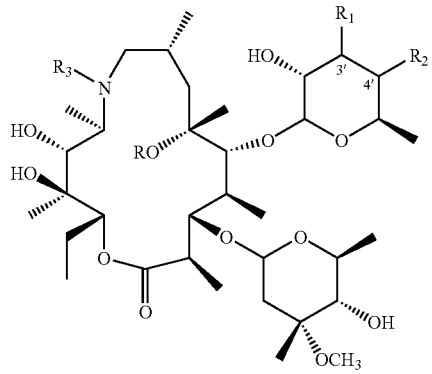

(II)

in which
R, $R_1$, $R_2$ and $R_3$ are defined as in claim 1.

12. A process according to claim 11 in which, in formula II, the substituent $R_3$ is a methyl.

13. A process according to claim 11 in which the removal of cladinose is effected through a reaction of catalyzed acid hydrolysis in the presence of an inorganic acid and a protic organic solvent.

14. A pharmaceutical composition containing a therapeutically effective quantity of a compound according to claim 1 mixed with a pharmaceutically acceptable vehicle.

15. A pharmaceutical composition according to claim 14 that can be used for treating inflammatory pathologies.

* * * * *